United States Patent
Santos

(10) Patent No.: US 8,362,209 B2
(45) Date of Patent: Jan. 29, 2013

(54) TELOMERASE REVERSE TRANSCRIPTASE VARIANT

(75) Inventor: Janine H. Santos, Dunellen, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 170 days.

(21) Appl. No.: 12/733,277

(22) PCT Filed: Aug. 25, 2008

(86) PCT No.: PCT/US2008/010076
§ 371 (c)(1),
(2), (4) Date: Mar. 30, 2010

(87) PCT Pub. No.: WO2009/025871
PCT Pub. Date: Feb. 26, 2009

(65) Prior Publication Data
US 2010/0247657 A1    Sep. 30, 2010

Related U.S. Application Data

(60) Provisional application No. 60/965,921, filed on Aug. 23, 2007.

(51) Int. Cl.
*C07K 16/00* (2006.01)
(52) U.S. Cl. ........................ 530/387.1; 530/350; 435/183
(58) Field of Classification Search ............... 530/387.1, 530/350; 435/183
See application file for complete search history.

(56) References Cited

U.S. PATENT DOCUMENTS
2007/0190561 A1    8/2007 Morin et al.

OTHER PUBLICATIONS

Seimiya et al. "Involvement of 14-3-3 proteins in nuclear localization of telomerase", The EMBO Journal, 2000, 19(11):2652-2661.*
Ahmed S. et al. (2008) Telomerase does not counteract telomere shortening but protects mitochondrial function under oxidative stress; Journal of Cell Science 121:1046-1053.
Del Bufalo, D. et al. (2005) Involvement of hTERT in apoptosis induced by interference with Bcl-2 expression and function; Cell Death & Differentiation 12:1429-1438.
Hertzog Santos, J., et al. (2004) Mitchondrial hTERT exacerbates free-radical-mediated mtDNA damage; Aging Cell, 3:399-411.
Hertzog Santos, J. et al (2006) Mitochondrial localization of telomerase as a determinant for hydrogen peroxide-induced mitochondrial DNA damage and apoptosis; Human Molecular Geneetics 15(11): 1757-1768.
Massard C. et al. (2006) hTERT: a novel endogenous inhibitor of the mitochondrial cell death pathway; Oncogene 25:4505-4514.

* cited by examiner

*Primary Examiner* — Susan Hanley
*Assistant Examiner* — Bin Shen
(74) *Attorney, Agent, or Firm* — Licata & Tyrrell P.C.

(57) ABSTRACT

The present invention relates to nucleic and amino acid sequences of a novel variant of the telomerase reverse transcriptase. More particularly, the present invention is directed to a novel variant of human telomerase reverse transcriptase, which displays properties distinct from those of wildtype telomerase reverse transcriptase, and methods of use thereof.

4 Claims, 10 Drawing Sheets

A

B

C control            L980A/L987AhTERTpCMV

A

B

A

B

B

C

A

B

D

TELOMERASE REVERSE TRANSCRIPTASE VARIANT

CROSS REFERENCE TO RELATED APPLICATIONS

The present application is a National Stage Application claiming the priority of co-pending PCT Application No. PCT/US2008/010076, filed Aug. 25, 2008, which in turn, claims priority from U.S. Provisional Application Ser. No. 60/965,921, filed Aug. 23, 2007. Applicants claim the benefits of 35 U.S.C. §120 as to the PCT application and priority under 35 U.S.C. §119 as to the said Provisional application, and the entire disclosures of both applications are incorporated herein by reference in their entireties.

FIELD OF THE INVENTION

The present invention is related to a novel variant of the telomerase reverse transcriptase gene and protein. More particularly, the present invention is directed to a novel variant of human telomerase reverse transcriptase, which displays properties distinct from those of wildtype telomerase reverse transcriptase and methods of use thereof.

BACKGROUND OF THE INVENTION

Several publications and patent documents are referenced in this application in order to more fully describe the state of the art to which this invention pertains. The disclosure of each of these publications and documents is incorporated by reference herein.

Telomeres, the protein-DNA structures physically located on the ends of the eukaryotic organisms, are required for chromosome stability and are involved in chromosomal organization within the nucleus (See e.g., Zakian, Science 270: 1601 [1995]; Blackburn and Gall, J. Mol. Biol., 120:33 [1978]; Oka et al., Gene 10:301 [1980]; and Klobutcher et al., Proc. Natl. Acad. Sci., 78:3015 [1981]). Telomeres are believed to be essential in such organisms as yeast and probably most other eukaryotes, as they allow cells to distinguish intact from broken chromosomes, protect chromosomes from degradation, and act as substrates for novel replication mechanisms. Telomeres are generally replicated in a complex, cell cycle and developmentally regulated manner by telomerase, a telomere-specific DNA polymerase. Telomerase-independent means for telomere maintenance have, however, been described. In that telomere loss is associated with chromosomal changes such as those that occur in cancer and aging, the study of telomeres and mechanisms contributing to their regulation have been at the center of intense investigations.

Telomeric DNA: In most organisms, telomeric DNA has been reported to consist of a tandem array of very simple sequences, which in many cases are short and precise. Typically, telomeres consist of simple repetitive sequences rich in G residues in the strand that runs 5' to 3' toward the chromosomal end. Heterogenous telomeric sequences have, however, been reported in some organisms. In addition, the repeated telomeric sequence in some organisms is much longer. The telomeric DNA sequences of many organisms have been determined (See e.g., Zakian, Science 270:1601 [1995]) and such studies have revealed that only limited consensus exists among these sequences (Zakian, supra). The average amount of telomeric DNA also varies among organisms. Moreover, in most organisms, the amount of telomeric DNA fluctuates. Heterogeneity and spontaneous changes in telomere length are thought to reflect a complex balance between the processes involved in degradation and lengthening of telomeric tracts. In addition, other factors including genetic and nutritional influences may cause increases or decreases in telomeric length (Lustig and Petes, Natl. Acad. Sci., 83:1398 [1986]; and Sandell et al., Cell 91:12061 [1994]). The inherent heterogeneity of virtually all telomeric DNAs suggests that telomeres are not maintained via conventional replicative processes.

Telomere Replication: Complete replication of the ends of linear eukaryotic chromosomes presents special problems for conventional methods of DNA replication. For example, conventional DNA polymerases cannot begin DNA synthesis de novo, rather, they require RNA primers which are later removed during replication. In the case of telomeres, removal of the RNA primer from the lagging-strand end would necessarily leave a 5'-terminal gap, resulting in the loss of sequence if the parental telomere was blunt-ended (Watson, Nature New Biol., 239:197 [1972]; Olovnikov, J. Theor. Biol., 41:181 [1973]). However, the described telomeres have 3' overhangs (Klobutcher et al., Proc. Natl. Acad. Sci., 58:3015 [1981]; Henderson and Blackburn, Mol. Cell. Biol., 9:345 [1989]; and Wellinger et al., Cell 72:51 [1993]). For these molecules, it is possible that removal of the lagging-strand 5'-terminal RNA primer could regenerate the 3' overhang without loss of sequence on this side of the molecule. Loss of sequence information on the leading-strand end would, however, occur due to the lack of a complementary strand to act as template in the synthesis of a 3' overhang (Zahler and Prescott, Nucleic Acids Res., 16:6953 [1988]; Lingner et al., Science 269:1533 [1995]).

While conventional DNA polymerases cannot accurately reproduce chromosomal DNA ends, specialized factors exist to ensure their complete replication. Telomerase (TERT) is a key component in this process. Telomerase is a ribonucleoprotein (RNP) particle and polymerase that uses a portion of its internal RNA moiety as a template for telomere repeat DNA synthesis (Yu et al., Nature 344:126 [1990]; Singer and Gottschling, Science 266:404 [1994]; Autexier and Greider, Genes Develop., 8:563 [1994]; Gilley et al., Genes Develop., 9:2214 [1995]; McEachern and Blackburn, Nature 367:403 [1995]; Blackburn, Ann. Rev. Biochem., 61:113 [1992]; Greider, Ann. Rev. Biochem., 65:337 [1996]). The activity of this enzyme depends upon both its RNA and protein components to circumvent the problems presented by end replication by using RNA (i.e., as opposed to DNA) to template the synthesis of telomeric DNA. Telomerases extend the G strand of telomeric DNA. A combination of factors, including telomerase processivity, frequency of action at individual telomeres, and the rate of degradation of telomeric DNA, contribute to the size of the telomeres (i.e., whether they are lengthened, shortened, or maintained at a certain size).

Notably, telomere replication is regulated both by developmental and cell cycle factors. It has been hypothesized that aspects of telomere replication may act as signals in the cell cycle. For example, certain DNA structures or DNA-protein complex formations may act as a checkpoint to indicate that chromosomal replication has been completed (See e.g., Wellinger et al., Mol. Cell. Biol. 13:4057 [1993]). In addition, it has been observed that in humans, telomerase activity is not detectable in most somatic tissues, although it is detected in many tumors (Wellinger, supra). Thus, telomere length may serve as a mitotic clock, which serves to limit the replication potential of cells in vivo and/or in vitro. In light of the contribution of telomerase to maintenance of telomere function and activity, telomerase is a bona fide target for development of agents directed to cancer therapy and/or slowing of aging processes.

SUMMARY OF THE INVENTION

Like other telomerases, human telomerase is composed minimally of two different subunits, a catalytic core (hTERT) and an RNA component (hTR). Together, they work in concert to replenish telomeres with every cell division. The present invention is directed to the discovery of a novel mutant of hTERT that exhibits altered functional activity with respect to wildtype hTERT.

In one aspect of the invention, the present inventor has generated a novel mutant of hTERT (L980A/L987AhTERT, also designated herein LAhTERT) that is excluded from the nucleus. Expression of L980A/L987AhTERT results in a delay in cell cycle progression and renders cells more sensitive to mitochondrial DNA (mtDNA) damage or apoptosis induced by hydrogen peroxide ($H_2O_2$) or by other types of oxidative stressors such as radiation treatment. These findings demonstrate that forced expression of the L980A/L987AhTERT mutant telomerase in cancer cells is a useful therapeutic strategy for slowing down tumor growth and increasing tumor sensitivity to genotoxic agents. The mutant can also be used to modulate diseases characterized by hyperplasia (high cellular growth rate).

Accordingly, the present invention is directed to an isolated nucleic acid sequence encoding a polypeptide comprising SEQ ID NO: 2 (L980A/L987AhTERT), or a functional fragment thereof, wherein said polypeptide exhibits an activity of L980A/L987AhTERT, for example, is capable of causing a delay in cell cycle progression and renders cells more sensitive to mtDNA damage or apoptosis induced by $H_2O_2$ or by other types of oxidative stressors such as radiation treatment. Also included are expression vectors comprising an isolated nucleic acid sequence which encodes an amino acid sequence of the invention (e.g., SEQ ID NO: 2), wherein expression of the nucleic acid sequence is controlled by regulatory sequences in an expression vector. Cells comprising such expression vectors are also encompassed. In yet another aspect, a transgenic animal/plant comprising an isolated nucleic acid sequence encoding a polypeptide comprising SEQ ID NO: 2, wherein the polypeptide is a L980A/L987AhTERT polypeptide or a functional fragment thereof, capable of exhibiting an activity of L980A/L987AhTERT, and the nucleic acid sequence is expressed in at least one cell of the transgenic animal/plant.

In another aspect of the invention, an isolated amino acid sequence comprising a polypeptide of SEQ ID NO: 2, or a functional fragment thereof, wherein said polypeptide is capable of exhibiting a L980A/L987AhTERT activity, is presented. As described herein, L980A/L987AhTERT activities include the ability to cause delayed cell cycle progression and the ability to render cells more sensitive to mtDNA damage or apoptosis induced $H_2O_2$ or by other types of oxidative stressors such as radiation treatment. Also included are expression vectors encoding an amino acid sequence of the invention (e.g., SEQ ID NO: 2), wherein expression of the amino acid sequence is controlled by regulatory sequences in the expression vector, cells comprising such expression vectors, and transgenic animals/plants comprising an amino acid sequence of the invention, wherein the amino acid sequence is expressed in at least one cell in the transgenic animal/plant.

In another aspect of the invention, an isolated nucleic acid sequence comprising SEQ ID NO: 1 is provided, wherein the nucleic acid sequence encodes L980A/L987AhTERT or a functional fragment thereof capable of exhibiting an activity attributable to L980A/L987AhTERT as described herein. Also described is an expression vector comprising a nucleic acid sequence of SEQ ID NO: 1, wherein the nucleic acid sequence encodes L980A/L987AhTERT or a functional fragment thereof capable of exhibiting an L980A/L987AhTERT activity, and SEQ ID NO: 1 is operably linked to a regulatory sequence. Moreover, a cell comprising such an expression vector is also within the scope of the invention. In another aspect, a transgenic animal/plant comprising a nucleic acid sequence comprising SEQ ID NO: 1, wherein the nucleic acid sequence encodes L980A/L987AhTERT or a functional fragment thereof capable of exhibiting an L980A/L987AhTERT activity, and wherein the nucleic acid sequence is expressed in at least one cell of the transgenic animal/plant is presented.

The present invention also encompasses an antibody immunologically specific for an amino acid sequence comprising SEQ ID NO: 2. Such antibodies can be polyclonal or monoclonal antibodies and functional fragments thereof.

The present invention also includes a kit comprising an isolated nucleic acid sequence comprising SEQ ID NO: 1, wherein the nucleic acid sequence encodes a L980A/L987AhTERT polypeptide or a functional fragment thereof; an isolated nucleic acid sequence encoding an amino acid sequence comprising SEQ ID NO: 2 or a functional fragment thereof; an isolated amino acid sequence comprising SEQ ID NO: 2, wherein the amino acid sequence is an L980A/L987AhTERT polypeptide or a functional fragment thereof; a L980A/L987AhTERT activity compatible buffer; at least one antibody immunologically specific for L980A/L987AhTERT; and instructional materials.

Also described is a composition comprising at least one L980A/L987AhTERT polypeptide or functional fragment thereof, an L980A/L987AhTERT encoding nucleic acid sequence, and at least one antibody immunologically specific for L980A/L987AhTERT identified using the methods of the invention and a pharmaceutically acceptable buffer. Compositions comprising a nucleic acid encoding the L980A/L987AhTERT polypeptide or a functional fragment thereof are also encompassed by the present invention.

Compositions containing the molecules or compounds of the invention can be administered for therapeutic purposes. In therapeutic applications, compositions comprising L980A/L987AhTERT or a functional fragment or derivative thereof are administered to a patient suffering from a hyperproliferative disorder (such as, e.g., cancer) in an amount sufficient to at least partially arrest or ameliorate the symptoms of the disease and its complications. An amount adequate to accomplish this is defined as a "therapeutically effective amount or dose". Compositions comprising a nucleic acid encoding the L980A/L987AhTERT polypeptide or a functional fragment or derivative thereof may also be used to deliver a therapeutically effective amount or dose of L980A/L987AhTERT or a functional fragment or derivative thereof to a patient in need thereof. Expression vectors comprising a nucleic acid encoding the L980A/L987AhTERT polypeptide or a functional fragment or derivative thereof are of utility for such therapeutic applications. Amounts effective for this use will depend on the severity of the disease and the weight and general state of the patient.

In an aspect of the invention, a method for treating a subject with a hyperproliferative disorder is presented that comprises administering to the subject a therapeutically effective amount of SEQ ID NO: 2 or a functional fragment or derivative thereof, wherein said administering achieves delivery of the SEQ ID NO: 2 or a functional fragment or derivative thereof to hyperproliferative cells in the subject, wherein said delivery causes delayed cell cycle progression in the hyperproliferative cells and/or increases sensitivity of the hyperproliferative cells to mitochondrial DNA damage or apoptosis induced by hydrogen peroxide or radiation treatment. Delaying cell cycle progression and/or increasing the sensitivity of the hyperproliferative cells to mitochondrial DNA damage or apoptosis induced by oxidative stressors (e.g., radiation) results in increased hyperproliferative cell death and this, in turn, leads to reduced numbers of hyperproliferative cells in the subject. In a particular aspect of the invention, the hyperproliferative disorder is a cancer. The method also encompasses combined therapy, wherein a therapeutically effective amount of SEQ ID NO: 2 or a functional fragment or derivative thereof is administered in conjunction with a genotoxic agent used to treat the hyperproliferative disorder.

In accordance with an aspect of the invention, the method calls for delivery of SEQ ID NO: 2 or a functional fragment or derivative thereof to hyperproliferative cells in the subject via administering the amino acid sequence of SEQ ID NO: 2 or a functional fragment or derivative thereof to said subject. In a particular embodiment, the amino acid sequence of SEQ ID NO: 2 or a functional fragment or derivative thereof is operably linked to an antibody or nanoparticle. Linkage to an antibody or nanoparticle may be used to target the attached amino acid sequence to a specific tissue or cell type.

In accordance with another aspect of the invention, the method calls for delivery of SEQ ID NO: 2 or a functional fragment or derivative thereof to hyperproliferative cells in the subject via administering a nucleic acid sequence encoding the amino acid sequence of SEQ ID NO: 2 or a functional fragment or derivative thereof to said subject. In a particular embodiment, an expression vector comprising said nucleic acid sequence encoding the amino acid sequence of SEQ ID NO: 2 or a functional fragment or derivative thereof is administered to said subject.

Inflammatory and/or autoimmune disorders are also treatable using the L980A/L987AhTERT mutant of the invention. In inflammatory and/or autoimmune disorders it is frequently desirable to eliminate some or all of the inflammatory or autoimmune cells. With respect to inflammatory disorders, inflammation is usually accompanied by oxidative stress. By targeting expression of the L980A/L987AhTERT mutant to inflammatory cells, for example, such cells would be triggered to die by apoptosis. Intervention via induced apoptosis would, therefore, limit the zone of inflammation and minimize the expansion of damage to surrounding areas of healthy tissue. Hepatitis, for example, wherein chronic oxidative stress caused by the virus can ultimately lead to carcinogenesis is a valid target for such an application.

The present invention also encompasses use of an isolated polypeptide comprising SEQ ID NO: 2 or a functional fragment or derivative thereof in the preparation of a medicament for the treatment of a hyperproliferative, inflammatory, or autoimmune disorder in a subject.

The present invention further encompasses use of an isolated nucleic acid sequence encoding SEQ ID NO: 2 or a functional fragment or derivative thereof in the preparation of a medicament for the treatment of a hyperproliferative, inflammatory, or autoimmune disorder in a subject.

Other features and advantages of the invention will be apparent from the following description of the preferred embodiments thereof, and from the claims.

total dead (floating cells) and viable cells (attached cells) were counted using a hemacytometer before and after the treatments.

Figure 6:
Figure 6:

FIG. 6. The cell cycle effects of L980A/L987AhTERT (LAhTERT) do not require telomerase enzymatic activity. (A) Telomerase enzymatic activity was assayed in NHF LAhTERT (lane 1) and NHF DNLAhTERT (DNL980A/L987AhTERT; lane 2). Positive and negative controls are omitted. (B). DNLAhTERT was stably expressed in NHF and cellular senescence gauged based on β-galactosidase activity. Dark gray cells represent cells positive for the senescent marker.

Figure 7:
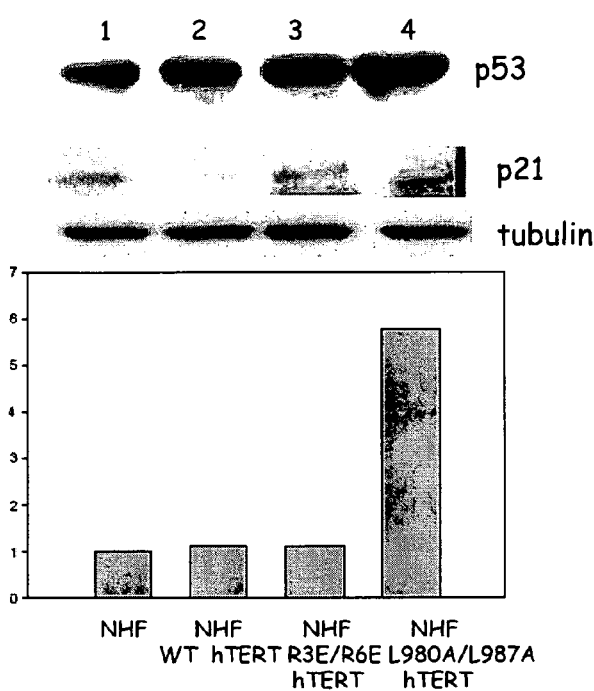
Figure 7:
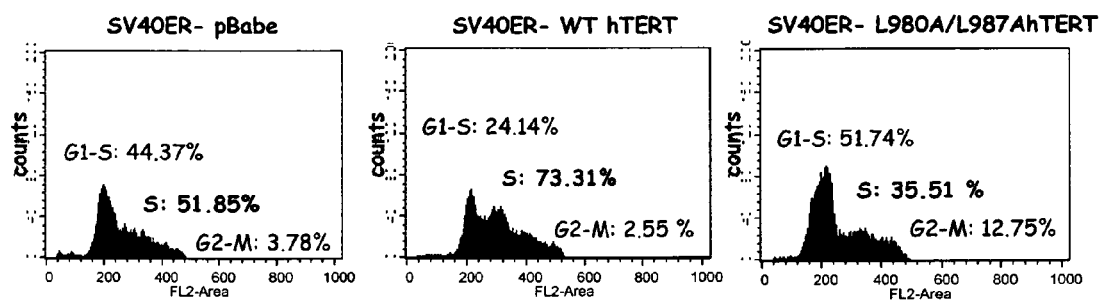

FIG. 7. Premature senescence caused by expression of L980A/L987AhTERT is partially dependent on the p53 pathway. (A) Western blots of whole cell extracts of NHF PD27 (lane 1), NHF hTERT (lane 2), NHF R3E/R6EhTERT (lane 3) and NHF L980A/L987AhTERT (lane were probed with anti-p53 or anti-p21 antibodies and for tubulin as a loading control. Lower panel show the relative amounts of p53 normalized to tubulin. (B) SV40ER-transformed fibroblasts were infected with empty pBabe vector, WT hTERT or L980A/L987AhTERT. Cells were synchronized by serum starvation, and released by the addition of serum to the medium; 8 h later cells were harvested, treated with RNase and PI, and submitted to flow cytometry. Data were collected with Cell Quest Software and percentage of cells in each phase of the cell cycle analyzed with ModFit. Data is representative of 2 independent experiments.

Figure 8:
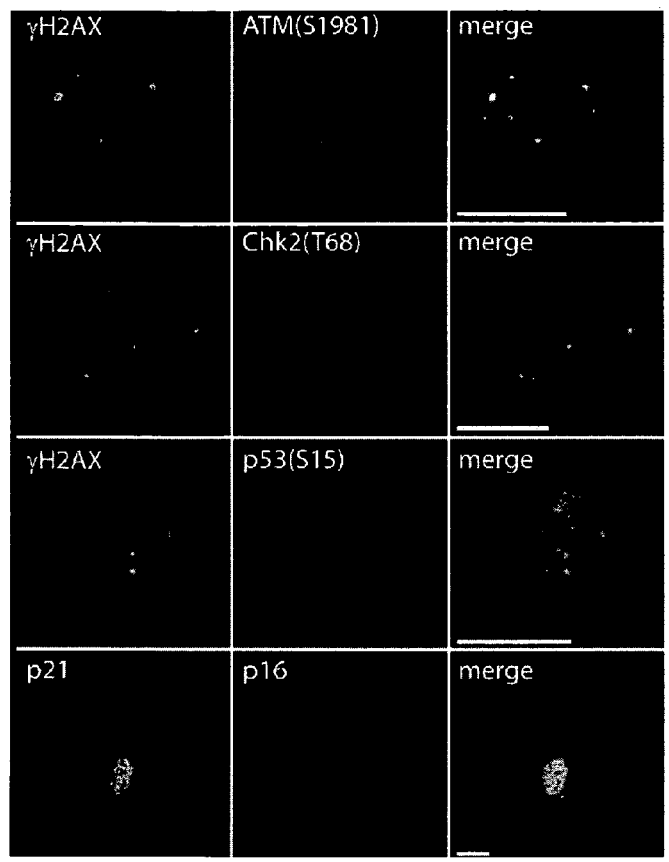
Figure 8:
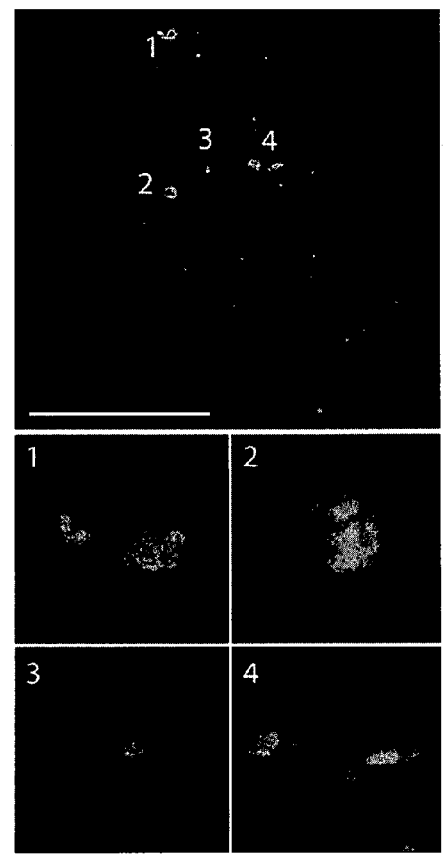
Figure 8:
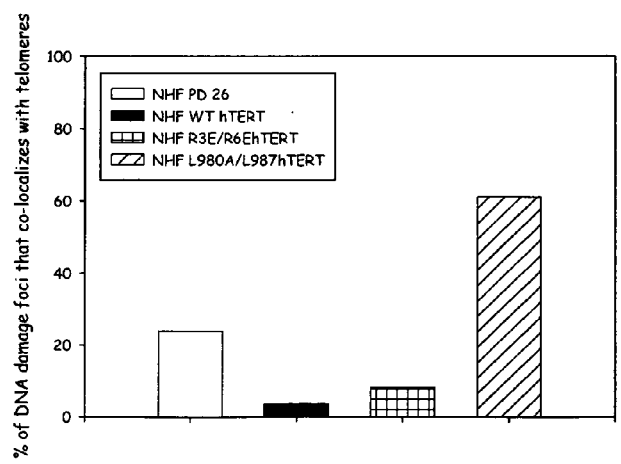

FIG. 8. L980A/L987AhTERT causes telomere dysfunction, phosphorylation of G1 DNA damage checkpoint proteins, and up-regulation of p21 and p16. (A) NHF expressing L980A/L987AhTERT were immunostained with antibodies against γH2AX (left panels, green) and phospho-ATM (S1981), phospho-Chk2(T68), and phosphor-p53(S15) (center panels, red). Bottom: the same cells were also immunostained with antibodies against the cyclin-dependent kinase inhibitors p21 (green) and p16 (red). DNA was counterstained with DAPI (blue). Merged images are shown in the right panels. (B) NHF L980 μL987AhTERT were processed by immunoFISH to simultaneously visualize γH2AX (green) and telomeres (red). DNA was counterstained with DAPI (blue). Enlarged versions of numbered γH2AX foci are shown in the bottom panels. Scale bar: 20 μm. (C) Graph shows percentage of total DNA damage foci that localized at telomeres (TIF).

Figure 9:
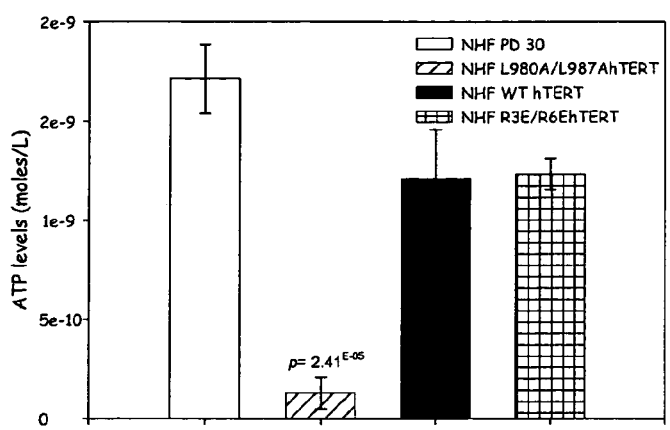
Figure 9:
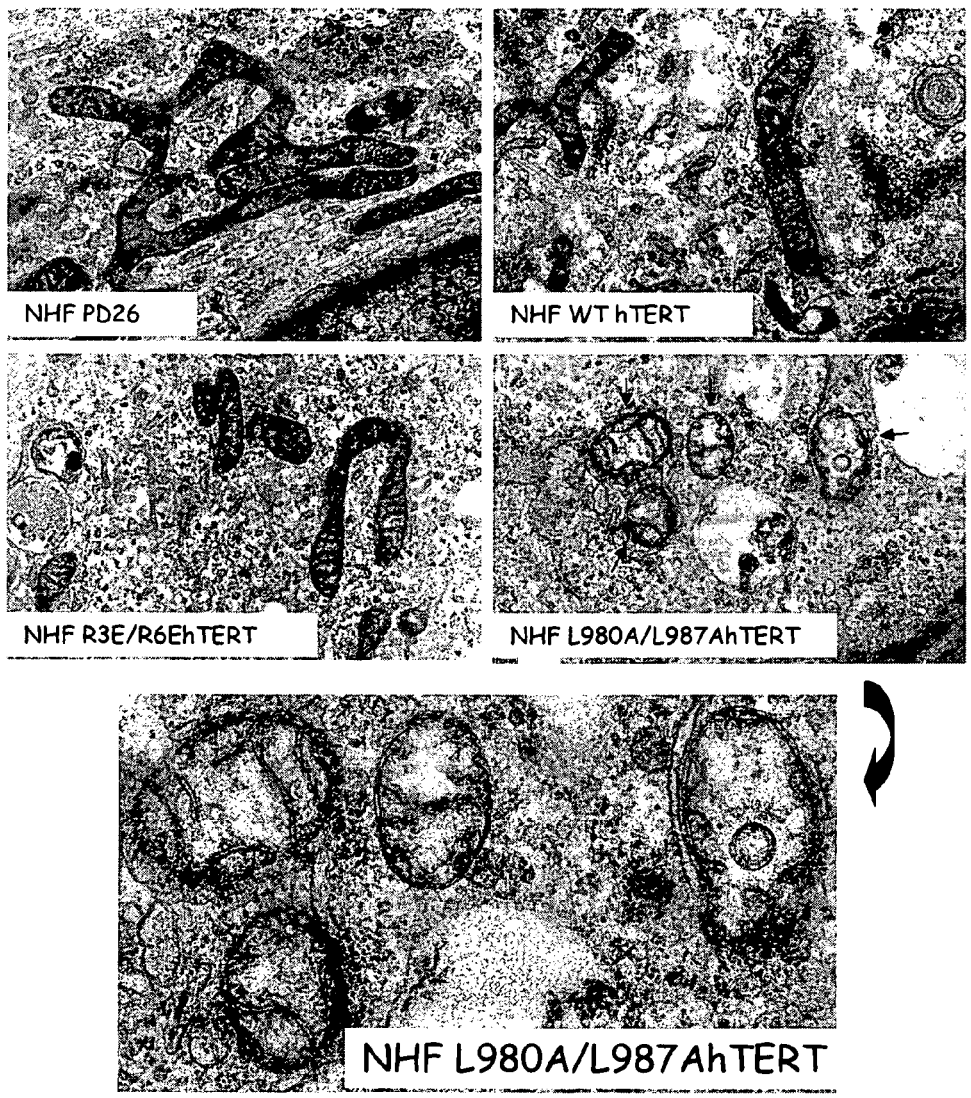
Figure 9:
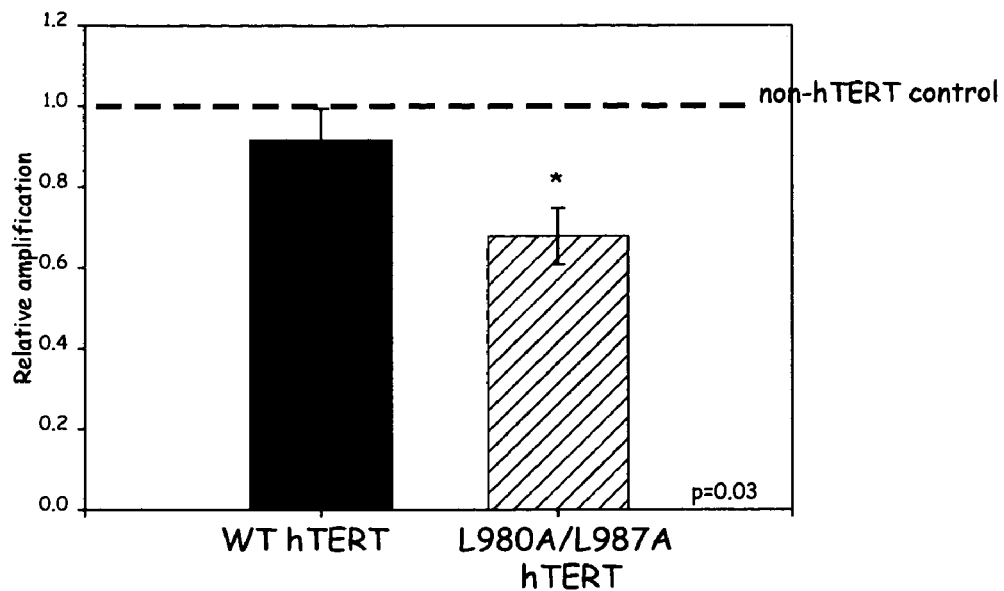
Figure 9:
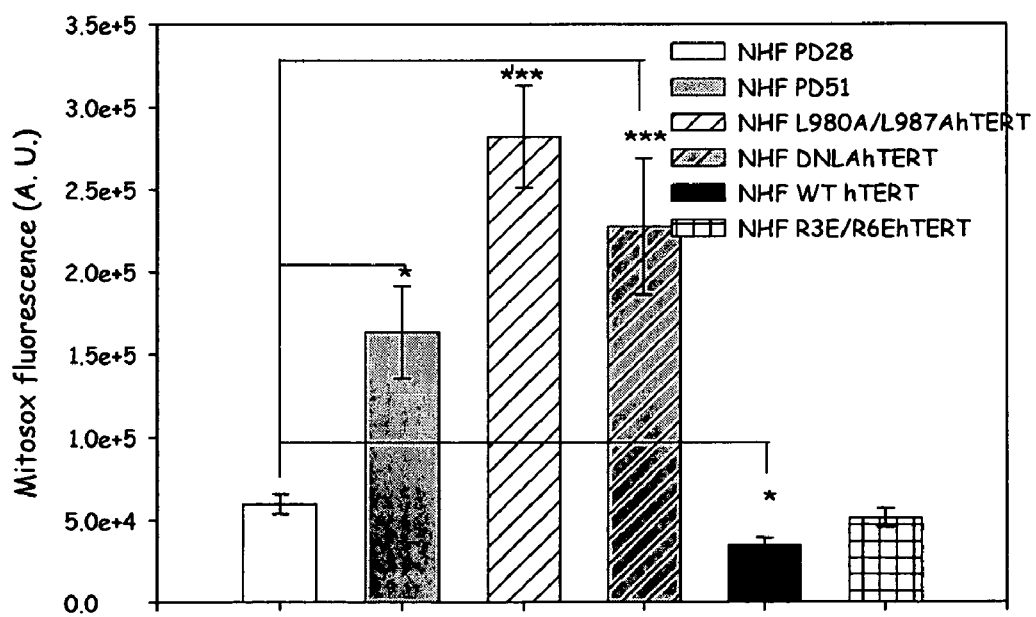

FIG. 9. Mitochondria of NHF L980A/L987AhTERT cells are highly dysfunctional. (A) Total ATP levels were measured using a luminometer in NHF and its hTERT derivatives. Equal numbers of cells were assayed; results represent average of triplicate experiments. A standard ATP curve was used to calculate the concentrations. Statistical significance was evaluated using Student's t test. *p=0.00002. No statistical difference was observed between NHF hTERT and R3E/R6EhTERT when compared to NHF. (B) NHF and its derivatives were analyzed by electron microscopy. (C) Total genomic DNA was obtained from SV40ER-transformed fibroblasts expressing empty pBabe vector, WT hTERT or LAhTERT. MtDNA content was estimated using gene-specific quantitative PCR as described in Santos et al. (2002) pp. 159-176 In W. C. Copeland (ed). Methods Mol. Biol.]). Average of 3 experiments±SEM is shown. Statistical significance was evaluated based on Student's t test. *p=0.03. (D) Levels of superoxide anion were estimated on NHF and its derivatives based on Mitosox fluorescence. Cells were seeded in coverslips 24 h prior to analysis and loaded with 1 μM for 10 min, washed and then analyzed using confocal microscopy. Image J software was used to calculate fluorescence intensity and background fluorescence was subtracted. Statistical significance was calculated using one way ANOVA. *p≦0.05; ***p≦0.0001. Senescent NHF (at PD 51) was included as control.

DETAILED DESCRIPTION OF THE INVENTION

As indicated herein above, telomerase adds DNA repeats to the ends of linear chromosomes thereby preventing telomere shortening. The enzyme contains two minimal components: an RNA subunit (TR), which provides the template for telomeric DNA synthesis, and a reverse transcriptase protein (TERT) that mediates catalysis [Shay et al. (2005) *Carcinogenesis*, 5, 867-874]. Telomerase is expressed in germ and undifferentiated somatic cells, and in over 90% of human cancers. Recent evidence suggests that it is transiently expressed in every adult somatic cell, at least in S-phase [Masutomi et al. (2003) *Cell*. 114, 241-253].

The present inventor and colleagues were the first to show that hTERT is also targeted to mitochondria [Santos et al. (2004) *Aging Cell*. 6, 399-411]; this observation has now been reproduced by independent laboratories [Del Bufalo et al. (2005) *Cell Death Differ*. 11, 1429-1438; Ahmed et al. (2008) *J Cell Sci*. 121, 1046-1053]. The presence of hTERT in mitochondria was surprising given the well established role of telomerase in telomere maintenance, and the lack of a telomeric structure on the mitochondrial DNA (mtDNA). These results were not, however, entirely unexpected as cytoplasmic localization of telomerase had been previously reported [Seimiya et al. (2000) *EMBO J*. 19, 2652-266; Armbruster et al. (2001) *Mol Cell Biol*. 22, 7775-7786; Haendeler et al. (2003) *Mol Cell Biol*. 13, 4598-610], and various studies suggest TERT's involvement in roles beyond telomere stabilization [Fu et al. (2002) *J Neurosci*. 22, 10710-10719; Baek et al. (2004) *Neurosci Lett*. 363, 94-96; Chung et al. (2005) *Curr Mol. Medicine*. 5, 233-241; Masutomi et al. (2005) *Proc. Natl. Acad. Sci. USA*. 102, 8222-8227; Sharma et al. (2003) *Oncogene* 22, 131-146; Gorbunova et al. (2002) *J. Biol. Chem*. 277, 38540-38549; Holt et al. (1999) *Mol. Carcinog*. 25, 241-248.23; Lee et al. (2005) *J. Cell Sci*. 118, 819-829; and Cong et al. (2008) *Cell Res*. 7, 725-732 for review].

The targeting of a single protein to more than one subcellular compartment, participating in different biochemical pathways and possibly with different cellular functions is well established [Regev-Rudzki et al. (2007) *Bioessays* 8, 772-782]. Examples of such proteins include Cu,Zn-superoxide dismutase (CuZnSOD) [Okado-Matsumoto et al. (2001) *J Biol. Chem*. 276, 38388-38393], fumarase [Sass et al. (2001) *J Biol. Chem*. 276, 46111-46117], aconitase [Klausner et al. (1993) *Mol Biol Cell*. 1, 1-5], and nucleoside diphosphate kinase [Amutha et al. (2003) *Biochem J*. 370, 805-315] known to be cytosolic and mitochondrial, adenylate kinase, which is cytoplasmic and plasma membrane-bound [Ruan et al. (2002) *Biophys J*. 6, 3177-3187], and DNA repair enzymes such as 8-oxoguanine DNA glycosylase (Ogg1) [Nakabeppu. (2001) *Prog Nucleic Acid Res Mol. Biol*. 68, 75-94] and Ku80 [Coffey et al. (2000) *Nucleic Acids Res*. 28, 3793-800] that are present both in the nucleus and in mitochondria. hTERT is thus another example of a dually-targeted and likely bifunctional protein.

The present inventor and colleagues showed that human cell lines expressing ectopic or endogenous hTERT exhibit increased mtDNA damage and decreased cellular viability after hydrogen peroxide ($H_2O_2$) treatment [Santos et al. (2004) *Aging Cell*. 6, 399-411; Santos et al. (2006) *Human Mol. Gen*. 15, 1757-1768]. Importantly, the present inventor demonstrated that the mitochondrial localization of hTERT is a key determinant for $H_2O_2$-induced mtDNA damage and apoptosis since expression of a nuclear-only mutant (R3E/R6EhTERT) which retains nuclear localization and function made cells resistant to cell death [Santos et al. (2006) *Human Mol. Gen.* 15, 1757-1768]. Previous work by others had also shown that forced expression of hTERT to the nucleus in conditions of oxidative stress was antiapoptotic [Haendeler et al. (2003) *Mol Cell Biol.* 13, 4598-610]. Thus, the subcellular localization of hTERT likely determines whether telomerase protects against- or sensitizes cells to reactive oxygen species (ROS). Shuttling of hTERT from nucleus to cytoplasm upon endogenous or exogenous oxidative stress had been reported [Haendeler et al. (2003) *Mol Cell Biol.* 13, 4598-610]. The relocalization of hTERT specifically to mitochondria under $H_2O_2$ or hyperoxia exposure has now been demonstrated [Ahmed et al. (2008) *J Cell Sci.* 121, 1046-1053]. Together, these data suggest that mitochondrial (re)localization is part of the normal biology of hTERT in response to changes in the cellular redox state.

Mitochondria not only generate ATP and ROS but also participate in a host of other important metabolic functions including the Krebs and urea cycles, β-oxidation, ketone-body synthesis, heme biosynthesis, iron-sulfur complex synthesis, calcium homeostasis and amino acid metabolism [Rehling et al. (2004) *Nat. Rev. Mol. Cell. Biol.* 7, 519-30]. Mitochondria are also centrally engaged in apoptosis [Green et al. (2004) *Science*, 305, 626-629]. Several lines of evidence demonstrate that dysfunction of mitochondria is linked to the process of aging and to various human disorders such as Parkinsonism, Alzheimer's disease and Leber's hereditary optic neuropathy [Orth et al. (2001) *Am. J. Med. Genet.* 106, 27-36]. A role for these organelles in the carcinogenic process has also been proposed [Copeland et al. (2002) *Cancer Invest.* 20:557-569]. Mitochondria have a circular DNA consisting of ~16 kb in mammals. The genome encodes 37 genes and 13 polypeptides involved in electron transport and ATP production [Croteau et al. (1999) *Mutat. Res.* 434, 137-148]. Integrity of the mtDNA tightly correlates to cell viability, i.e., increased mtDNA repair enhances cell survival following oxidative stress. Conversely, loss or uncoupling of DNA repair capacity and subsequent mtDNA integrity can lead to cell death and human disease [Van Houten et al. (2006) *DNA Repair*, 5, 145-152].

To better understand the role of hTERT in mitochondria, the present inventor created a mutant in which the nuclear export signal (NES) of hTERT is mutated. Surprisingly, stable expression of this mutant in normal human fibroblasts (NHF) caused premature senescence. The molecular events associated with L980A/L987AhTERT-provoked premature senescence, which involves activation of DNA damage response (DDR) genes such as ATM, Chk2 and p53, and up-regulation of the cyclin-dependent kinase inhibitors $p21^{CIP1/WAF1}$ and $p16^{INK4a}$, are described herein. Nuclear DNA damage primarily at the telomeres is also observed. L980A/L987AhTERT cells have dysfunctional mitochondria and show increased ROS production, establishing a direct link between L980A/L987AhTERT-driven mitochondrial impairment and nuclear DNA damage. These findings strongly support the idea that hTERT is not only dually-targeted but it is also a bifunctional protein. Coupled with our previous observations [Santos et al. (2006) *Human Mol Gen.* 15, 1757-1768], the instant data suggest that hTERT participates in a pathway involved in cell cycle decisions, triggering growth arrest or apoptosis depending on the cellular redox state. Further, they demonstrate a novel mechanism for oncogene-induced senescence that relies initially on mitochondrial dysfunction.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As noted above, the terms used herein have the meanings recognized and known to those of skill in the art. However, for convenience and completeness, particular terms and their meanings are set forth below.

As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

The term "complementary" refers to two DNA strands that exhibit substantial normal base pairing characteristics. Complementary DNA may, however, contain one or more mismatches.

The term "hybridization" refers to the hydrogen bonding that occurs between two complementary DNA strands.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it is generally associated in its natural state (i.e., in cells or tissues). An isolated nucleic acid (either DNA or RNA) may further represent a molecule produced directly by biological or synthetic means and separated from other components present during its production.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 60%, but often, more than 85%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

The terms "percent similarity", "percent identity" and "percent homology" when referring to a particular sequence are used as set forth in the University of Wisconsin GCG software program and are known in the art.

The present invention also includes active portions, fragments, derivatives and functional or non-functional mimetics of a mutant hTERT polypeptide or protein of the invention. An "active portion" of a mutant hTERT polypeptide refers to a peptide that is less than the full length mutant hTERT polypeptide, but which retains measurable biological activity.

A "fragment" or "portion" of a mutant hTERT polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. A "derivative" of the mutant hTERT polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, and may or may not alter the essential activity of the original mutant hTERT polypeptide.

Different "variants" of the mutant hTERT polypeptide may be generated. The skilled person can produce variants having single or multiple amino acid substitutions, deletions, additions or replacements. These variants may include inter alia: (a) variants in which one or more amino acids residues are substituted with conservative or non-conservative amino acids, (b) variants in which one or more amino acids are added to the mutant hTERT polypeptide, (c) variants in which one or more amino acids include a substituent group, and (d) variants in which the mutant hTERT polypeptide is fused with another peptide or polypeptide such as a fusion partner, a protein tag or other chemical moiety, that may confer useful properties to the mutant hTERT polypeptide, such as, for example, an epitope for an antibody, a polyhistidine sequence, a biotin moiety and the like. Other mutant hTERT polypeptides of the invention include variants in which amino acid residues from one species are substituted for the corresponding residue in another species, either at conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to a person having ordinary skill in the art.

To the extent such analogues, fragments, derivatives, mutants, and modifications, including alternative nucleic acid processing forms and alternative post-translational modification forms result in derivatives of a mutant hTERT polypeptide that retain any of the biological properties characteristic of the mutant hTERT polypeptide, they are included within the scope of this invention.

The term "functional" as used herein implies that the nucleic or amino acid sequence is functional for the recited assay or purpose.

The term "functional fragment" as used herein implies that the nucleic or amino acid sequence is a portion or subdomain of a full length polypeptide and is functional for the recited assay or purpose.

The phrase "consisting essentially of" when referring to a particular nucleotide or amino acid means a sequence having the properties of a given SEQ ID No. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the term "operably linked" refers to a regulatory sequence capable of mediating the expression of a coding sequence and which is included in a DNA molecule (e.g., an expression vector) in an appropriate position relative to the coding sequence so as to effect expression of the coding sequence. This same definition is sometimes applied to the arrangement of coding sequences and transcription control elements (e.g., promoters, enhancers, and termination elements) in an expression vector. This definition is also sometimes applied to the arrangement of nucleic acid sequences of a first and a second nucleic acid molecule wherein a hybrid nucleic acid molecule is generated.

As used herein, the terms "nucleic acid", "polynucleotide" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites). There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA.

The term "oligonucleotide," as used herein may be used to refer to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

RNA interference (RNAi) is an evolutionarily conserved mechanism in plant and animal cells that directs the degradation of messenger RNAs homologous to short double-stranded RNAs termed "small interfering RNA" or "siRNA" or "short hairpin RNA" or "shRNA". The ability of siRNA to direct gene silencing in mammalian cells has raised the possibility that siRNA might be used to investigate gene function in a high throughput fashion or to modulate gene expression in human diseases. Methods of preparing siRNAs are known to those skilled in the art. The following references are incorporated herein by reference in their entirety: Reich et al., *Mol Vis.* 9:210-6 (2003); Gonzalez-Alegre P et al., *Ann Neurol.* 53:781-7 (2003); Miller et al., *Proc Natl Acad Sci USA.* (2003); Bidere et al., *J Biol. Chem.*, published as manuscript M301911200 (Jun. 2, 2003); Van De Wetering et al., EMBO Rep. 4:609-15 (2003); Miller and Grollman, *DNA Repair (Amst)* 2:759-63 (2003); Kawakami et al., *Nat Cell Biol.* 5:513-9 (2003); Abdelrahim et al. *Mol. Pharmacol.* 63:1373-81 (2003); Williams et al., *J Immunol.* 170:5354-8 (2003); Daude et al., *J Cell Sci.* 116:2775-9 (2003); Jackson et al., *Nat. Biotechnol.* 21:635-7 (2003); Dillin, *Proc Natl Acad Sci USA.* 100:6289-91 (2003); Matta et al., *Cancer Biol Ther.* 2:206-10 (2003); Wohlbold et al., *Blood.* (2003); Julien and Herr, *EMBO J.* 22:2360-9 (2003); Scherr et al., *Cell Cycle.* 2:251-7 (2003); Giri et al., *J Immunol.* 170:5281-94 (2003); Liu and Erikson, *Proc Natl Acad Sci USA.* 100:5789-94 (2003); Chi et al., *Proc Natl Acad Sci USA.* 100:6343-6 (2003); Hall and Alexander, *J. Virol.* 77:6066-9 (2003).

"Antisense" nucleic acids are DNA or RNA molecules that are complementary to at least a portion of a specific mRNA molecule (See Weintraub, Sci. *Amer.* 262:40-46 (1990); Marcus-Sekura, *Nucl. Acid Res,* 15: 5749-5763 (1987); Marcus-Sekura *Anal. Biochem.,* 172:289-295 (1988); Brysch et al., *Cell Mol. Neurobiol.,* 14:557-568 (1994)). In the cell, the single stranded antisense molecule hybridizes to that mRNA, forming a double stranded molecule. The cell does not translate an mRNA in this double-stranded form. Therefore, antisense nucleic acids interfere with the expression of mRNA into protein. Oligomers of greater than about fifteen nucleotides and molecules that hybridize to the AUG initiation codon will be particularly efficient. Antisense methods have been used to inhibit the expression of many genes in vitro (Marcus-Sekura, *Anal. Biochem.,* 172:289-295 (1988); Hambor et al., *Proc. Natl. Acad. Sci. U.S.A.* 85:4010-4014 (1988)) and in situ (Arima et al., Antisense Nucl. Acid Drug Dev. 8:319-327 (1998); Hou et al., *Antisense Nucl. Acid Drug Dev.* 8:295-308 (1998)).

Splicing variants of hTERT that exhibit, for example, nuclear or mitochondrial localization and are, therefore, physically separated at the RNA level can be targeted differentially using techniques such as those described above with respect to siRNA.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Primers may be labeled fluorescently with 6-carboxyfluorescein (6-FAM). Alternatively primers may be labeled with 4, 7, 2', 7'-Tetrachloro-6-carboxyfluorescein (TET). Other alternative DNA labeling methods are known in the art and are contemplated to be within the scope of the invention.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like). "Mature protein" or "mature polypeptide" shall mean a polypeptide possessing the sequence of the polypeptide after any processing events that normally occur to the polypeptide during the course of its genesis, such as proteolytic processing from a polypeptide precursor. In designating the sequence or boundaries of a mature protein, the first amino acid of the mature protein sequence is designated as amino acid residue 1.

The term "tag", "tag sequence" or "protein tag" refers to a chemical moiety, either a nucleotide, oligonucleotide, polynucleotide or an amino acid, peptide or protein or other chemical, that when added to another sequence, provides additional utility or confers useful properties to the sequence, particularly with regard to methods relating to the detection or isolation of the sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxyterminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

The terms "transform", "transfect", "transduce", shall refer to any method or means by which a nucleic acid is introduced into a cell or host organism and may be used interchangeably to convey the same meaning. Such methods include, but are not limited to, viral infection, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other applications, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

As used herein, the term "hyperproliferative cells" refers to cells with uncontrolled proliferation or abnormally high proliferative rates. A "hyperproliferative disorder" is a disorder or condition characterized by the presence of hyperproliferative cells or cells having a high cellular growth rate.

As used herein, the term "cancer" refers to an abnormal growth of tissue resulting from uncontrolled progressive multiplication of cells. Examples of cancers that can be treated according to a method of the present invention include, without limitation, sarcomas, adenomas, blastomas, and carcinomas such as: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, gastric cancer, pancreatic cancer, breast cancer, meningeal carcinomatosis (which is most commonly associated with disseminated breast or lung cancer), ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, liver metastases, bile duct carcinoma, choriocarcinoma, seminoma, embryonal carcinoma, thyroid carcinoma such as anaplastic thyroid cancer, Wilms' tumor, cervical cancer, testicular cancer, lung carcinoma such as small cell lung carcinoma and non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, acinic cell carcinoma, acoustic neuroma, acral lentiginous melanoma, acrospiroma, adamantinoma, adrenocortical cancer, adenoid cystic carcinoma, adenomatoid odontogenic tumor, adrenocortical carcinoma, allograft diseases, alveolar soft part sarcoma, ameloblastic fibroma, anal cancer, angiomyolipoma, bowel cancer, bone tumor, Brenner tumor, bronchioloalveolar carcinoma, brown tumor, carcinoma in situ (CIS), carcinoma of the penis, cervical intraepithelial neoplasia, granulocytic sarcoma, cholangiocarcinoma, chondroma, chondrosarcoma, chordoma, choriocarcinoma, choroid plexus papilloma, clear cell tumor, colorectal cancer, craniopharyngioma, Dermatofibrosarcoma protuberans, dermoid cyst, desmoid tumor, desmoplastic small round cell tumor, ductal carcinoma, dysembryoplastic neuroepithelial tumour, car cancer, embryonal carcinoma, endodermal sinus tumor, endometrial cancer, endometrioid tumor, ependymoma, esophageal cancer, extramammary Paget's disease (EMPD), eye cancer, gallbladder cancer, ganglioneuroma, gastrointestinal cancer, gastrointestinal stromal tumor, germ cell tumor, germinoma, gestational choriocarcinoma, giant cell tumor of bone, glioblastoma multiforme, glioma, gliomatosis cerebri, glomus tumor, glucagonoma, granulosa cell tumour, hairy cell leukemia, head and neck cancer, heart cancer, hemangioblastoma, hemangiopericytoma, hemangiosarcoma, hepatocellular carcinoma, inflammatory breast cancer, islet cell carcinoma, Kaposi's sarcoma, Klatskin tumor, Krukenberg tumor, laryngeal cancer, lentigo maligna melanoma, liposarcoma, liver cancer, lymphangioma, lymphangiosarcoma, lymphoepithelioma, malignant fibrous histiocytoma, malignant peripheral nerve sheath tumor, mediastinal germ cell tumor, mediastinal tumor, medulloblastoma, melanoma, meningioma, merkel cell cancer, mixed Mullerian tumor, mucinous tumor, nasopharyngeal carcinoma, neurofibroma, neuroma, Nodular melanoma, oligoastrocytoma, oligodendroglioma, oncocytoma, optic nerve sheath meningioma, oral cancer, Paget's disease of the breast, Pancoast tumor, pancreatic cancer, paraganglioma, pinealocytoma, pituicytoma, pituitary adenoma, pituitary tumour, pleuropulmonary blastoma, primary peritoneal cancer, pseudomyxoma peritonei, renal cell carcinoma, Richter's transformation, sacrococcygeal teratoma, Schwannomatosis, Sertoli-Leydig cell tumour, small intestine cancer, soft tissue sarcoma, somatostatinoma, spinal tumor, stomach cancer, superficial spreading melanoma, surface epithelial-stromal tumor, uterus cancer, vaginal cancer and Waldenstrom's macroglobulinemia. The diseases listed above can be treated in any stage, from hyperproliferative benign state to metastatic variants.

Examples of hematologic malignancies that can be treated according to a method of the present invention include: acute myeloid leukemia (AML), chronic myeloid leukemia (CML), acute lymphocytic leukemia (ALL), chronic lymphocytic leukemia (CLL), multiple myeloma, non-Hodgkin's lymphoma (NHL), Hodgkin's disease and lymphoma (HD), prolymphocytic leukemia (PLL), myelodysplastic syndrome (MDS), adult T-cell leukemia, aggressive NK-cell leukemia, anaplastic large cell lymphoma, angioimmunoblastic T-cell lymphoma, Burkitt's lymphoma, chronic neutrophilic leukemia, cutaneous T cell lymphoma, erythroleukemia, follicular lymphoma, gastric lymphoma, hepatosplenic T-cell lymphoma, juvenile Myelomonocytic Leukemia (JMML), primary central nervous system lymphoma, primary effusion lymphoma, and splenic marginal zone lymphoma In short, any disorder characterized by a hallmark hyperplasia, which, therefore, exhibits hyperproliferation of cells can be ameliorated using the L980A/L987AhTERT mutant. The above list is included for reference only and is not intended to be comprehensive, because hyperplasia is observed in most tissues/organs. Additional examples include: congenital hyperplasia of retinal pigment epithelium, prostate hyperplasia, and hyperplasia of the endocrine system, including primary and secondary hyperplasia of the endocrine system. Primary hyperplasia includes: thyroid hyperplasia (thyroid hormones and also c-cell hyperplasia-calcitonin production), parathyroid gland hyperplasia, pituitary gland, adrenal gland, suprarenal gland, pancreatic β-cell hyperplasia. Secondary hyperplasia includes circumstances wherein a lesion in one endocrine organ (such as abnormal trophic stimulus and/or change in negative feedback control) leads to long term stimulation and hyperproduction of a target organ. Examples include: adrenal cortex secondary hyperplasia, wherein abnormal trophic stimulus leads to corticotrophic adenoma (ACTH excess), hypertrophy/hyperplasy (zona fasciculata), and cortizol-excess syndrome ("Cushing disease"). Multiple endocrine neoplasia type 1 (MEN 1), also known as Wermer's Syndrome, falls within the category of syndromes treatable using the mutant of the invention. Hyperparathyroidism and pituitary adenomas, the majority of which secrete prolactin, with or without secretion of excess A prolactinoma may also be treated with the L980A/L987AhTERT mutant.

As used herein, the term "mtDNA damage" refers to damage present on the mtDNA that leads to loss of integrity of the genome. Examples of such damage include, without limitation, DNA lesions such as base oxidations, DNA single or double strand breaks, abasic sites, methylation of the DNA, nick or gaps on the DNA, intrastrand or interstrand cross links, addition of bulky lesions, and deletions.

As used herein, the term "oxidative damage" refers to damage that is incurred by an oxidative stressor, which therefore involves an oxygen or a radical derivative, and leads to features of oxidation. With respect to DNA, this usually refers to base oxidation and breaks on the DNA strands. With respect to proteins, it involves oxidation of particular amino acids leading to, for instance, protein carbonyls. With respect to lipids/membranes, it relates to oxidation of lipid chains leading to a cascade of further oxidative events (called lipid peroxidation).

As used herein, the term "oxidative stressor" refers to an agent capable of causing oxidative damage.

As used herein, "increased sensitivity" when used with respect to targets of oxidative damage (in this case the mtDNA or the cell as a whole) means that the targets are damaged to a greater extent than a control population of targets following exposure to an oxidative stressor. In short, targets of oxidative damage have a threshold of resistance to the damage incurred by such stressors. Increased sensitivity to an oxidative stressor, therefore, means that the balance shifts to a lower threshold and thus exposure to the same stressor leads to more damage as compared to a control population. With respect to the present invention, increased sensitivity of the mtDNA means that the same exposure to a stressor leads to higher levels of damage or, in other words, the mtDNA becomes less resistant to oxidative stress. As a consequence, cells comprising mtDNA having increased sensitivity to oxidative stress also become more sensitive and, therefore, die after exposure to a lower dose of the oxidative stressor relative to the dose that would be required to kill cells having mtDNA with normal sensitivity to oxidative stress.

In accordance with the present invention, increased sensitivity to oxidative damage reflects that once an oxidative stressor is applied, cells that express hTERT (or LAhTERT in this case) will be more damaged (in terms of mtDNA), which is associated with higher levels of cell death.

Figure 4:
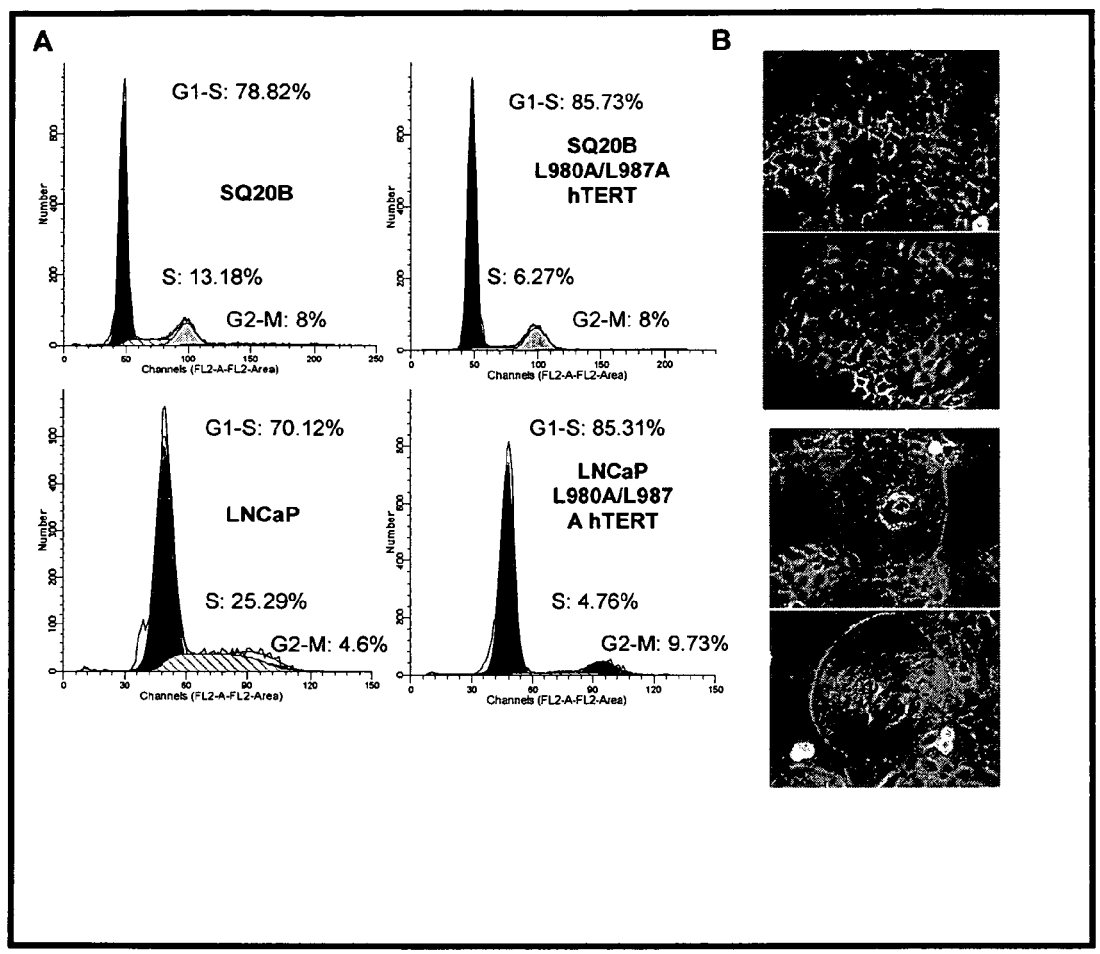
FIG. 4. Expression of L980A/L987AhTERT alters cell cycle of cancer cells. (A) Cell cycle analysis was performed using propidium iodide (PI). Cells were synchronized by serum starvation overnight. Serum was added to the medium and 8 h after cells were harvested, treated with RNase and PI, and submitted to flow cytometry analysis. Upper panels show SQ20B before and after introduction of L980A/L987A hTERT (squamous carcinoma cells). Lower panels represent LNCaP (prostate cancer) cells (wild type and after introduction of L980A/L987AhTERT). (B) Cell morphology of SQ20B and SQ20B carrying L980A/L987AhTERT 72 h after cells were plated. Note that the same number of cells was seeded in each dish. Phase contrast images are shown. Two upper panels show control SQ20B; lower panels represent SQ20B carrying L980A/L987AhTERT.

As used herein, the phrase "effects a delay in cell cycle progression" refers to the ability of an agent (e.g., LAhTERT) to slow cell cycle progression when expressed in a cell. In other words, a cell that expresses LAhTERT will undergo a slower cell cycle progression relative to a matched control cell that does not express LAhTERT. Delayed cell cycle progression in LAhTERT expressing cells relative to matched control cells is shown, for example, in FIG. 4. Broadly speaking, cell cycle progression refers to the transitions from cell cycle stages G1-S, to M, to G2-S. Thus, a delay in cell cycle progression observed in LAhTERT expressing cells is reflected in an increased percentage of these cells that remain in G1-S or S phase relative to a matched control cell population.

The present invention is applicable to any mammal and thus may be used for veterinary purposes. The high sequence/function conservation observed among species, particularly among mouse, rat and human TERT supports applicability of efficacious use of the L980A/L987AhTERT mutant broadly in mammalian species. The subject is preferably an animal, including but not limited to animals such as monkeys, cows, pigs, horses, chickens, cats, dogs, etc., and is particularly a mammal, and more particularly human. In one specific embodiment, a non-human mammal is the subject. In another specific embodiment, a human mammal is the subject.

With respect to targeted delivery of the therapeutic mutant hTERT of the invention, a skilled practitioner can use antibodies, viral infections, the TAT sequence from the HIV virus to target the protein to the mitochondria within cells, and nanoparticles to achieve locale specific or localized delivery.

Nanotechnology refers to the use of man-made nano-sized (typically 1-100 billionths of a meter) particles for industrial or medical applications suited to their unique properties. With respect to medical applications, nanoparticles are particles that are a hundred to ten thousand times smaller than human cells. They are similar in size to large biological molecules ("biomolecules") such as enzymes and receptors. Because of their small size, nanoscale devices can readily interact with biomolecules on both the surface and inside of cells. By gaining access to so many areas of the body, they have the potential to detect disease and deliver treatment to virtually any bodily locale.

Many different types of nanoparticles are currently being studied for applications in nanomedicine. They can be carbon-based skeletal-type structures, such as the fullerenes, or micelle-like, lipid-based liposomes, which are already in use for numerous applications in drug delivery and the cosmetic industry. Colloids, typically liposome nanoparticles, selected for their solubility and suspension properties are used in cosmetics, creams, protective coatings and stain-resistant clothing. Other examples of carbon-based nanoparticles are chitosan and alginate-based nanoparticles, which are described in the literature for oral delivery of proteins, and various polymers under study for insulin delivery. Additional nanoparticles can be made from metals and other inorganic materials, such as phosphates. Nanoparticle contrast agents are compounds that enhance magnetic resonance imaging (MRI) and ultrasound results in biomedical applications of in vivo imaging. These particles typically contain metals whose properties are dramatically altered at the nano-scale. Gold "nanoshells" are useful in the fight against cancer, particularly soft-tissue tumors, because of their ability to absorb radiation at certain wavelengths. Once the nanoshells enter tumor cells and radiation treatment is applied, they absorb the energy and heat up enough to kill the cancer cells. Positively-charged silver nanoparticles adsorb onto single-stranded DNA and are used for its detection. Many other tools and devices for in vivo imaging (fluorescence detection systems), and to improve contrast in ultrasound and MRI images, are being developed.

A more detailed description of some nanoparticle types is presented below:

Fullerenes: Buckyballs and Carbon Tubes

Both members of the fullerene structural class, buckyballs and carbon tubes are carbon based, lattice-like, potentially porous molecules. Buckyballs are spherical in shape, while carbon tubes are cylindrical. The diameter of a carbon tube can be several nanometers, but the length can be much greater, up to several millimeters, depending on its intended use. Carbon tubes have many applications in materials science due to their strength and unique electrical properties. They have, however, also found use in the field of biomedicine as carriers for vaccines, drugs and other molecules. A single wall carbon tube is a one-atom-thick sheet of graphite, resembling chicken wire and rolled seamlessly into a tube. There are also multi-walled tubes and other types of tubes depending on the shape, diameter, density (hollow versus solid) and other properties of the tube.

Liposomes

Liposomes are lipid-based nanoparticles used extensively in the pharmaceutical and cosmetic industries because of their capacity to break down inside cells, once their delivery function has been met. Liposomes are the first engineered nanoparticles used for drug delivery, but problems such as their propensity to fuse together in aqueous environments and release their payload, have lead to their replacement or stabilization using newer alternative nanoparticles.

Nanoshells

Also referred to as core-shells, nanoshells are spherical cores of a particular compound surrounded by a shell or outer coating of another, which is a few nanometers thick. One application in biomedicine is to create nanoshells that absorb at biologically useful wavelengths, depending on the shell thickness. One common formula for the construction of nanoshells is to use silica for the core and another sticky compound to adhere gold particles to the outside surface, creating the shell. Nanoshells such as these have been used to kill cancer cells in mice. Once injected into a tumor, radiation is applied and the nanoshells heat up enough to kill the tumor cells.

Dendrimers

Dendrimers are highly branched structures that are gaining wide use in nanomedicine because of the multiple molecular "hooks" on their surfaces that can be used to attach cell-identification tags, fluorescent dyes, enzymes and other molecules. The first dendritic molecules were produced around 1980, but interest in them has blossomed more recently as biotechnological uses are discovered. Nanomedical applications for dendrimers are many and include nanoscale catalysts and reaction vessels, micelle mimics, imaging agents and chemical sensors, and agents for delivering drugs or genes into cells. There are two basic structural types of dendrimers. The first type possesses a globular structure with a central core from which branches radiate. The second type has no central core and consists simply of a series of highly branched polymers.

Quantum Dots

Also known as nanocrystals, quantum dots are nanosized semiconductors that, depending on their size, can emit light in all colors of the rainbow. These nanostructures confine conduction band electrons, valence band holes, or excitons in all three spatial directions. Examples of quantum dots are semiconductor nanocrystals and core-shell nanocrystals, wherein there is an interface between different semiconductor materials. They have been applied in biotechnology for cell labelling and imaging, particularly in cancer imaging studies.

Superparamagnetic Nanoparticles

Superparamagnetic molecules are attracted to a magnetic field, but do not retain residual magnetism after the field is removed. Nanoparticles of iron oxide with diameters in the 5-100 nm range, have been used for selective magnetic bio-separations. Typical techniques involve coating the particles with antibodies to cell-specific antigens, for subsequent separation from the surrounding matrix. Used in membrane transport studies, superparamagenetic iron oxide nanoparticles (SPION) are applied for drug delivery and gene transfection. Targeted delivery of drugs, bioactive molecules or DNA vectors is dependent on the application of an external magnetic force that accelerates and directs their progress towards the target tissue. They are also useful as MRI contrast agents.

Nanorods

Typically 1-100 nm in length, nanorods are most often made from semiconducting materials and used in nanomedicine as imaging and contrast agents. Nanorods can be made by generating small cylinders of silicon, gold or inorganic phosphate, among other materials.

As indicated herein, treatments may be achieved by administering DNA encoding the hTERT mutant of the invention in an expressible genetic construct. DNA encoding the hTERT mutant of the invention may be administered to the patient using techniques known in the art for delivering DNA to the cells. Retroviral vectors, electroporation or liposomes, for example, may be used to deliver DNA.

An "immune response" signifies any reaction produced by an antigen, such as a protein antigen, in a host having a functioning immune system. Immune responses may be either humoral, involving production of immunoglobulins or antibodies, or cellular, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunloglobulin molecule such as those portions known in the art as Fab, Fab', F(ab')$_2$ and F(v).

Exemplary epitopes of the mutant hTERT of the present invention that can be used to generate an antibody immunologically specific for the mutant hTERT (i.e., an antibody that only recognizes this mutant) are also encompassed herein. Such an antibody would not, therefore, be immunologically specific for wildtype hTERT or other mutant hTERTs.

hTERT nucleic acids or a fragment thereof comprising such an L980A/L987AhTERT mutant specific epitope are also encompassed herein. hTERT nucleic acids or a fragment thereof can comprise a C-terminal Cys or no terminal modifications. Fragments of hTERT include N-terminal fragments [H] and C-terminal fragments [OH]. Immunological purity should be 50% or greater. Antigenic epitopes should, in general, be hydrophilic and have a size range of at least 8 amino acids, so as to encompass the two amino acid substitutions. Particular L980A/L987AhTERT mutant specific epitopes are indicated in bold and underlined as follows: VLR AKSHSLFADLQC (SEQ ID NO: 5) and RRKLFGVLR AKCHSLFAC (SEQ ID NO: 6).

The term "control substance", "control agent", or "control compound" as used herein refers a molecule that is inert or has no activity relating to an ability to modulate a biological activity. With respect to the present invention, such control substances are inert with respect to an ability to modulate a mutant hTERT activity and/or a signaling pathway that contributes to an activity of a mutant hTERT. Exemplary controls include, but are not limited to, solutions comprising physiological salt concentrations. In addition, as indicated in the Example sections, vector controls such as the empty vector, an unrelated protein (such as EGFP) or the same mutant that is enzymatically inactive (at least when assayed in vitro) are also encompassed herein.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated. Accordingly, the phrase "therapeutically effective amount" is used herein to mean an amount sufficient to reduce by at least about 15 percent, preferably by at least 50 percent, more preferably by at least 90 percent a clinically significant deficit in the activity, function and response of the host. Alternatively, a therapeutically effective amount is sufficient to cause an improvement in one or more clinically significant symptoms in the host.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both.

Pharmaceutical Compositions

When employed as pharmaceuticals, the polypeptides of this invention are typically administered in the form of a pharmaceutical composition. Such compositions can be prepared in a manner well known in the pharmaceutical art and comprise at least one active compound.

Generally, the polypeptides of the invention (or DNA encoding a polypeptide of the invention) are administered in a pharmaceutically effective amount. The amount of the polypeptide or DNA encoding same actually administered will typically be determined by a physician, in the light of the relevant circumstances, including the condition to be treated, the chosen route of administration, the actual polypeptide or DNA administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the polypeptides of this invention, for example, are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or polypeptides of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The polypeptides of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The polypeptides of this invention can also be administered in sustained release forms or from sustained release drug delivery systems. A description of representative sustained release materials can be found in *Remington's Pharmaceutical Sciences.*

The following formulation examples illustrate representative pharmaceutical compositions of this invention. The present invention, however, is not limited to the following pharmaceutical compositions.

Formulation 1—Tablets

A polypeptide of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2—Capsules

A polypeptide of the invention is admixed as a dry powder with a starch diluent in an approximate 1:1 weight ratio. The mixture is filled into 250 mg capsules (125 mg of active amide compound per capsule).

Formulation 3—Liquid

A polypeptide of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A polypeptide of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5—Injection

A polypeptide of the invention is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present polypeptides or DNA encoding a polypeptide of the invention are used as therapeutic agents for the treatment of conditions in mammals that are associated with elevated levels of cellular proliferation such as those characteristic of hyperproliferative disorders (e.g., psoriasis) and cancers. As described herein, the polypeptides of the invention delay cell cycle progression and render cells more sensitive to oxidative stress as evidenced by increased sensitivity to both mtDNA damage and apoptosis induced by hydrogen peroxide or radiation treatment. These properties render cancer cells, for example, more susceptible to the toxic effects of radiation and other genotoxic agents commonly used to treat cancer in a patient. Accordingly, the polypeptides and pharmaceutical compositions of this invention find use as therapeutics for treating a variety of cancers and hyperproliferative conditions in mammals, including humans.

With respect to the ability of the hTERT mutant polypeptide to render cells more sensitive to oxidative stress, it is noteworthy that several cancer-inducing agents fall within the category oxidative stressors. Such oxidative stressors include: mitochondrial inhibitors (such as paraquat and menadione), glucose deprivation, hyperoxia, ischemia reperfusion, TNFα, some environmental pollutants that are associated with oxidative stress including hexavalent chromium, potassium bromide and asbestos, metal ions such as lead, iron, cadmium, mercury and copper, hydrogen peroxide, superoxide anion, enzymes (such as xantine or glucose oxidases, cytochrome P450s, superoxide dismutase), UV radiation, pro-oxidants such as vitamin E, homocysteine; and those produced by the immune system (produced by, e.g., macrophages), or induced by bacterial infection (any type of inflammatory response), or hormones (such as estrogen).

Methods for treating cancer that can be used to advantage in combination with the mutant hTERT of the invention include every chemotherapeutic/antineoplastic drug that is known to induce oxidative stress. The following categories are presented, without limitation: anthracyclines, most alkylating agents, platinum-coordination complexes, epipodophyllotoxins, camptothecins, taxanes, vinca alkaloids, antifolates, and nucleoside and nucleotide analogues. Examples of such drugs are as follows: etoposide, doxorubicin, tamoxifen, bleomycin, adryamycin, daunomycin, mitoxantrone, cisplatin, emodin/arsenic trioxide; hyperoxia, mitomycin C, carmustine (BCNU), cyclophosphamide, busolfan, actinomycin D, AraC, daunorubicin, 6-hydroxydopamine, paclitaxel, methotrexate, motexafin gadolinium, and ionizing radiation (which is frequently used in breast cancer therapy). Avoiding anti-oxidants, which scavenge the oxygen radicals, is also a strategy that can be used in combination with the compositions and/or methods of the present invention.

In a method of treatment aspect, this invention provides a method of treating a mammal afflicted with cancer or a condition associated with a hyperproliferative disorder, which method comprises administering an effective amount of one or more of the pharmaceutical compositions just described.

As a further aspect of the invention the present polypeptides are provided for use as a pharmaceutical especially in the treatment of the aforementioned conditions and diseases. Also provided herein is the use of the present polypeptides in the manufacture of a medicament for the treatment of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the treatment of long-term hyperplasic conditions, such as, for example: psoriasis, endometrium hyperplasia, hyperplasia of the thyroid, muscle hyperplasia, and dandruff (caused by hyperplasia of the skin on the scalp), the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg. Alternatively, the delivery system can be via antibody- or nanoparticle-mediated targeting to specific cell types and/or compartments.

Transdermal doses are generally selected to provide similar or lower blood levels than are achieved using injection doses.

The polypeptides of this invention can be administered as the sole active agent or they can be administered in combination with other agents, including other polypeptides that demonstrate the same or a similar therapeutic activity, and that are determined to safe and efficacious for such combined administration.

Expression Vectors

A gene encoding an hTERT mutant of the invention, active fragment or derivative thereof, can be introduced either in vivo, ex vivo, or in vitro in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. For example, in the treatment of neurological disorders or injuries, the striatal subventricular zone (SVZ) can be specifically targeted. Examples of particular vectors include, but are not limited to, a defective herpes virus 1 (HSV1) vector (Kaplitt et al., *Molec. Cell. Neurosci.*, 2:320-330 (1991)), an attenuated adenovirus vector, such as the vector described by Stratford-Perricaudet et al. (*J. Clin. Invest.*, 90:626-630 (1992)), and a defective adeno-associated virus vector (Samulski et al., *J. Virol.*, 61:3096-3101 (1987); Samulski et al., *J. Virol.*, 63:3822-3828 (1989)) including a defective adeno-associated virus vector with a tissue specific promoter, (see e.g., U.S. Pat. No. 6,040,172, Issued Mar. 21, 2000, the contents of which are hereby incorporated by reference in their entireties).

In another embodiment, an hTERT mutant of the invention can be introduced in a retroviral vector, e.g., as described in U.S. Pat. No. 5,399,346; Mann et al., (1983) *Cell*, 33:153; U.S. Pat. No. 4,650,764; U.S. Pat. No. 4,980,289; Markowitz et al., (1988) *J. Virol.*, 62:1120; U.S. Pat. No. 5,124,263; International Patent Publication No. WO 95/07358, published Mar. 16, 1995; and Kuo et al., (1993) *Blood*, 82:845.

Targeted gene delivery is described in International Patent Publication WO 95/28494, published October 1995.

Alternatively, the vector can be introduced by lipofection. Liposomes may be used for encapsulation and transfection of nucleic acids in vitro. Synthetic cationic lipids designed to limit the difficulties and dangers encountered with liposome mediated transfection can be used to prepare liposomes for in vivo transfection of an hTERT mutant of the invention, active fragment or derivative thereof (Felgner, et. al., *Proc. Natl. Acad. Sci. U.S.A.*, 84:7413-7417 (1987); see Mackey, et al., *Proc. Natl. Acad. Sci. U.S.A.*, 85:8027-8031 (1988)). The use of cationic lipids may promote encapsulation of negatively charged nucleic acids, and also promote fusion with negatively charged cell membranes (Felgner and Ringold, *Science*, 337:387-388 (1989)). The use of lipofection to introduce exogenous genes into the specific organs in vivo has certain practical advantages. Molecular targeting of liposomes to specific cells represents one area of benefit. It is clear that directing transfection to particular cell types is particularly advantageous in a tissue with cellular heterogeneity, such as the brain. Lipids may be chemically coupled to other molecules for the purpose of targeting (see Mackey et. al., *Proc. Natl. Acad. Sci. U.S.A.*, 85:8027-8031 (1988)).

It is also possible to introduce the vector as a naked DNA plasmid. Naked DNA vectors for short term or long term gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., (1992) *J. Biol. Chem.*, 267:963-967; Wu and Wu, (1988) *J. Biol. Chem.*, 263:14621-14624; Hartmut et al., Canadian Patent Application No. 2,012,311, filed Mar. 15, 1990).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

Aspects of the Invention

Before the present discovery and methods of use thereof are described, it is to be understood that this invention is not limited to particular assay methods, or test compounds and experimental conditions described, as such methods and compounds may vary. It is also to be understood that the terminology used herein is for the purpose of describing particular embodiments only, and is not intended to be limiting, since the scope of the present invention will be limited only the appended claims.

EXAMPLES

Materials and Methods

Cell Culture. Primary normal human fibroblasts (NHF) and their respective hTERT-pBabe derivatives were described and maintained as in Santos et al. [Santos et al. (2006) *Human Mol. Gen.* 15, 1757-1768]. Human fibroblasts transformed with the early region of simian virus 40 (SV40ER, GM847) were a kind gift of Dr. Robert Weinberg (Whitehead Institute, MIT); cells were maintained as described in reference [Stewart et al. (2002) *Proc Natl Acad Sci USA*. 99, 12606-12611]. HeLa, HEK 293T, LNCaP, PA317 and PT67 cells were all obtained from ATCC. SQ20B were a gift from Dr. Edouard Azzam (New Jersey Medical School). Cells were grown in Dulbecco's modified Eagle high glucose medium (Gibco/Invitrogen) supplemented with 10% fetal bovine serum and 1% penicillin and streptomycin.

Plasmids. Retroviral pBabe vectors with different hTERT mutants and pCMV-20AAhTERT-EGFP vector were described earlier [Santos et al. (2004) *Aging Cell.* 6, 399-411; Santos et al. (2006) *Human Mol. Gen.* 15, 1757-1768]. For stable expression of the latter, the first 20 amino acids of hTERT fused to EGFP were subcloned into the pLXIN retroviral vector. L980/L987AhTERT was generated by site-directed mutagenesis of wild type hTERT in both EGFP and pBabe vectors [Santos et al. (2004) *Aging Cell.* 6, 399-411; Santos et al. (2006) *Human Mol. Gen.* 15, 1757-1768] by replacing leucine residues at position 980 and 987 for alanine (L980A/L987A hTERT). This mutant was also subcloned into the pCMV vector for transient transfections. Dominant negative L980/L987AhTERT (pBabe DN L980/L987AhTERT or DNLAhTERT) was constructed by replacing the 2.5 KB BamHI fragment in pBabe L980/L987AhTERT by the 2.5 KB BamHI fragment from dominant negative hTERT (Addgene, plasmid 1775). This plasmid was previously described by Hahn and co-workers [Hahn et al. (1999) *Nat. Med.* 10, 1164-1170]. All constructs were sequenced to assure introduction of the mutations. Transient and stable transfections were performed as described previously [Santos et al. (2004) *Aging Cell.* 6, 399-411; Santos et al. (2006) *Human Mol. Gen.* 15, 1757-1768].

Cell cycle analysis. Normal and SV40ER-transformed fibroblasts (and respective hTERT derivatives) were serum starved overnight and released from serum starvation by addition of 10% FBS into the medium for 8 hours. Cell cycle analysis by flow cytometry with propidium iodide (PI, Molecular Probes) was performed as described by previously [Santos et al. (2003) *J Biol. Chem.* 278, 1728-1734] using a BD Biosciences FACSCalibur flow cytometer. DNA content analysis was performed by Modi Fit LT (Verify Inc.) software.

Analysis of Senescence. NHF and its derivatives were plated on 60 mm dishes and stained for senescence-associated β-galactosidase activity using staining kit (Cell Signaling) according to the manufacturer's protocol.

$H_2O_2$ treatments, DNA isolation and analysis of integrity by Quantitative PCR (QPCR). $H_2O_2$ (Sigma) treatments were performed as described earlier [Santos et al. (2003) *J. Biol. Chem.* 278, 1728-1734]. After treatments, cells were washed twice and harvested immediately for DNA analysis. High molecular weight DNA was extracted and QPCR performed and analyzed as described previously [Santos et al. (2002) pp. 159-176 In W. C. Copeland (ed). Methods Mol. Biol.]. Large fragments of both nuclear and mitochondrial genomes were amplified; the primers sequence can be found elsewhere [Santos et al. (2002) pp. 159-176 In W. C. Copeland (ed). Methods Mol. Biol.]. A small (139 bp) fragment of the mtDNA was also amplified, and was used to monitor mitochondrial copy number and to normalize results obtained with the large fragment (for more details see [Santos et al. (2002) pp. 159-176 In W. C. Copeland (ed). Methods Mol. Biol.]).

Telomeric Repeat Amplification Protocol (TRAP). 100 or 500 ng of total protein extracts were assayed for TRAP using TRAPeze kit (Chemicon) according to manufacturer's instructions and with some modifications [Santos et al. (2004) *Aging Cell.* 6, 399-411; Santos et al. (2006) *Human Mol. Gen.* 15, 1757-1768].

Apoptosis and cell death/viability assays. YOPRO-1 (Molecular Probes) was used to evaluate the percentage of apoptotic cells in control and treated samples. Cells were analyzed immediately after treatments and 24 h after recovery. During apoptosis the cytoplasmic membrane becomes slightly permeant. Certain dyes, such as the green fluorescent YO-PRO®-1 dye can enter apoptotic cells, whereas other dyes, such as the red fluorescent dye, propidium iodide (PI), cannot. Thus, use of YO-PRO®-1 dye and PI together provide a sensitive indicator for apoptosis [Agrelo et al. (2006) *Proc Natl Acad Sci USA* 103, 8822-8827; Chin et al. (2004) *Nat Genet.* 36, 984-988]. Data presented were confirmed with both Hoescht incorporation as well as caspase-3 activation.

Western blot analysis for cell cycle check point proteins. Whole cell extracts from NHF and its hTERT derivatives were subjected to Western blot analysis for p53 (BD Biofarmingen) and p21 (Calbiochem) proteins according to manufacturer's instructions, α-tubulin (Sigma) was used as a loading control. Approximately 20 μg of total protein were loaded/lane.

Immunofluorescence of DDR, p21 and p16 proteins. Cells were grown on coverslips for at least 48 h prior to immunostaining. After washing with PBS, cells were fixed for 20 min with 4% paraformaldehyde/PBS, permeabilized for 20 min with PBST (PBS containing 0.2% Triton X-100), and blocked for 1 h with PBS/4% BSA. Cells were incubated with antibodies, diluted in blocking buffer, for 2 h at room temperature, followed by three 5 min washes with PBS. The secondary Alexa-488-(Invitrogen) and Cy3-(Jackson Immunoresearch) conjugated antibodies were diluted 1:1000 in blocking buffer and added to the cells for 1 h in a humidified chamber. After two 5 min washes with PBS cells were mounted using DAPI containing mounting media (Vector). Primary antibodies were used at following dilutions: anti-γH2AX(S139) (Upstate), anti-p21 (C-19, Santa Cruz), anti-p16 (JC8, Abcam), 1:1000; anti-ATM(S1981) (Abcam), 1:200; anti-Chk2(T68) (Lot 1, Cell Signaling), 1:500; anti-p53(S15) (Cell Signaling), 1:100. Images were acquired using a Zeiss Axiovert 200 fluorescence microscope equipped with ApoTome.

ImmunoFISH. Cells were processed and stained with anti γH2AX antibodies as described above. Following three 5 min washes with PBS, the cells were incubated with Alexa-488 conjugated rabbit anti mouse antibodies diluted 1:1000 in PBS for 1 h. After two 5 min washes with PBS, the cells were incubated with 4% paraformaldehyde/PBS for 20 min, washed 2×5 min with PBS, and dehydrated by sequentially placing them in 70%, 90%, and 100% ethanol for 3 min each. Nuclear DNA was denatured for 5 min at 80° C. in hybridization buffer containing 0.5 μg/ml $(C_3TA_2)_3$-Cy3-labeled peptide nucleic acid (PNA), 70% formamide, 12 mM Tris-HCl (pH8), 5 mM KCl, 1 mM $MgCl_2$, 0.001% Triton X-100, and 2.5 mg/ml acetylated BSA. After denaturation, incubation was continued for 2 h at room temperature in a humidified chamber. Cells were washed two times for 15 min with 70% formamide/2 SSC (0.3 M NaCl, 30 mM Na-Citrate (pH 7), followed by a 10 min wash with 2×SSC and a 10 min wash with PBST. To reinforce the protein signal, cells were incubated for 1 hr with an Alexa-488 conjugated goat anti-rabbit secondary antibody. Cells were mounted as described above and analyzed by immunofluorescence microscopy using a Zeiss Axiovert 200 fluorescence microscope equipped with ApoTome. Images were acquired as z-stacks spaced 0.4 μm apart using a 100× lens with 1.4 optical aperture.

ATP measurements. ATP production in NHF cells and derivatives was measured with the ATP Bioluminescent Assay kit (Sigma) according to the manufacturer's instructions with a standard curve being created to precise measurement of ATP. Each experiment was repeated at least 3 times.

Electron microscopy. NHF and its hTERT derivative were processed in sections (approximately 1 $mm^3$), which were rapidly fixed in diluted Karnovsky's. Embedded sections (0.5 μm) were cut with a glass knife and stained with Toluidine blue for orientation. Ultrathin sections were cut with a diamond knife, stained with uranyl acetate and lead citrate and viewed on a Philips Morgagni electron microscope (Philips, Amsterdam NL). Structurally damaged mitochondria were operationally defined as having loss or dissolution of ≧25% of cristae, alteration of size and vacuolization. Number of mitochondria per cell was also evaluated.

Mitosox measurements. Superoxide levels in NHF cells and derivatives were monitored by live imaging confocal microscopy based on MitoSox Red (Invitrogen) fluorescence. Cells were plated on glass coverslips 48 h prior to the experiment, incubated at 37° C. for 10 minutes with 1 μM of mitosox diluted in HBSS buffer. After incubation, the fluorescent indicator was removed and cells were washed with warm HBSS buffer. Images were acquired using laser scanning confocal microscope (Radiance 2000; Bio-Rad Hercules, Calif., USA) connected to a Zeiss Axiovert 1000 inverted microscope. At least 10 images were taken and approximately 50 cells analyzed/coverslip for each cell type. Approximately 300 cells/cell type were analyzed in at least three independent experiments. Total MitoSox Red fluorescent intensity was calculated using Image) software; background fluorescence values were subtracted.

Statistical analysis. Unpaired or paired student's t-test and one-way ANOVA were used to calculate statistical significance as described in figure legends; p≦0.05 was considered significant.

Results

The present inventor observed increased levels of mitochondrial DNA (mtDNA) damage and apoptosis in cells expressing wild type (WT) hTERT after exposure to hydrogen peroxide ($H_2O_2$) [Santos et al. (2004) Aging Cell 3, 399-411]. More recently, the inventor demonstrated that these effects are dependent on the presence and activity of hTERT in mitochondria [Santos et al. (2006) Hum Mol. Genet. 15, 1757-1768]. In fact, use of a nuclear-only hTERT mutant, which has the mitochondrial targeting abolished but its nuclear localization and activity unaffected, render cells resistant to oxidative stress [Santos et al. (2006) Hum Mol. Genet. 15, 1757-1768]. These observations led the present inventor to investigate whether the subcellular localization of hTERT (nuclear and/or mitochondrial) differentially impacts the carcinogenic process. In addition, the inventor hypothesized that forced expression of hTERT out of the nucleus and potentially into mitochondria of cancer cells would increase their response to genotoxic stress. With this in mind, a mutant of hTERT having an altered nuclear export signal (NES) was generated as described below.

By way of background, a NES had been previously identified in hTERT. Moreover, mutation of 3 residues in this region promoted CRM1/exportin, a receptor for the nuclear export machinery, binding to the TERT NES-like motif, thereby exporting TERT from the nucleus to the cytoplasm [Seimiya et al. (2000) EMBO J. 19, 2652-266]. Using site-directed mutagenesis, therefore, the present inventor altered two amino acid residues of the NES [Seimiya et al. (2000) EMBO J. 19, 2652-2661] of hTERT. More specifically, leucine residues at position 980 and 987 were substituted by alanine, rendering L980A/L987AhTERT. Subcellular localization of the protein was analyzed in stable transfectants using an anti-hTERT antibody (from Rockland Immunochemicals).

The subregion of wild type (WT) hTERT and the NES mutant (L980A/L987A hTERT) wherein the mutations were made are shown below:

```
                                                    (SEQ ID NO: 7)
N-terminus . . .
RRKLFGVLRLKCHSLFLDLQVNSLQTVCTN . . . WT hTERT (SEQ ID NO: 8)
N-terminus . . .
RRKLFGVLRAKCHSLFADLQVNSLQTVCTN . . . L980A/L987A
                                       hTERT
```

LAhTERT does not support growth of colonies in soft agar. Stewart and co-workers [(2002) Proc. Natl. Acad. Sci. USA. 99, 12606-12611] have shown that telomerase is a key component that renders cells tumorigenic. Using cell lines that maintain their telomeres independently of telomerase, they demonstrated that both p53 inactivation and/or RasV12 overexpression were not sufficient to permit cell growth in soft agar or to make tumors when injected in nude mice. In fact, only the presence of telomerase allowed cells to grow in both systems. These observations led to the conclusion that telomerase contributes to tumorigenesis by a telomere length-independent mechanism.

Figure 1:
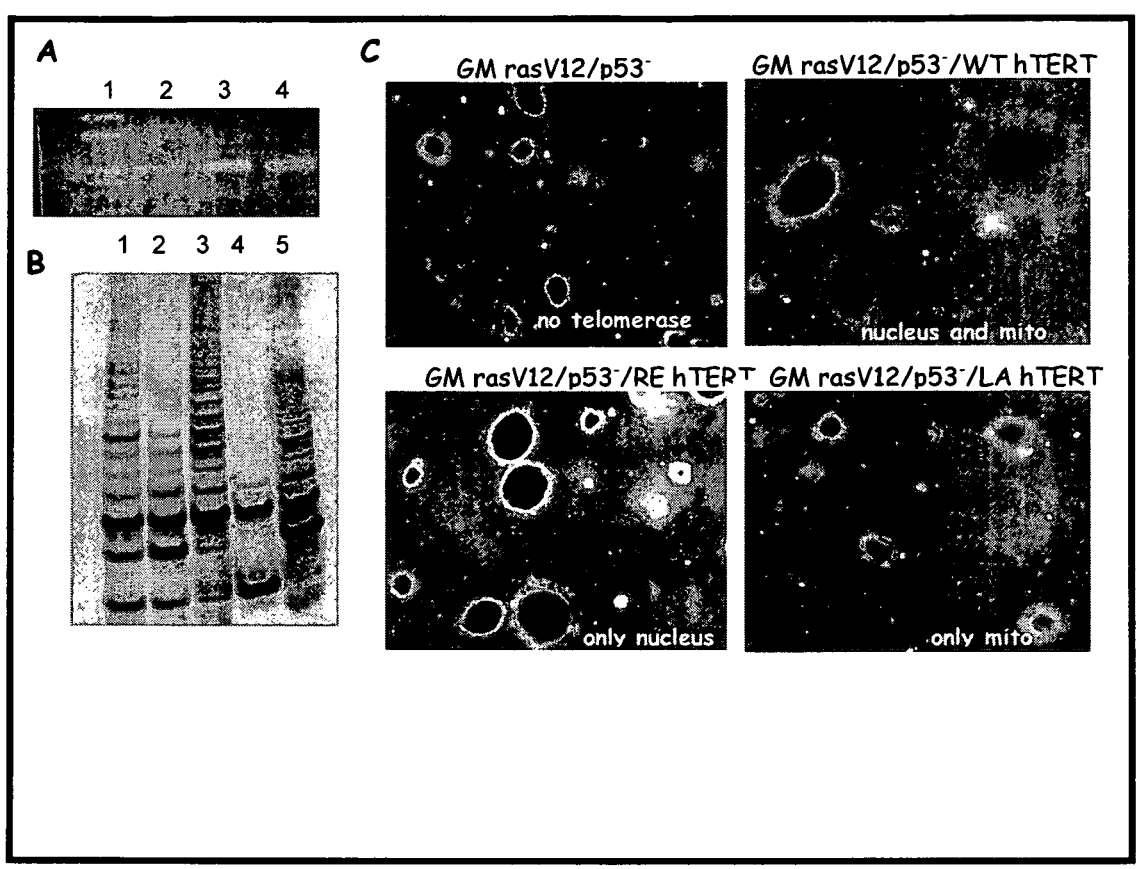
FIG. 1. L980/L987AhTERT is expressed and active, and does not support colony growth in soft agar. (A) Total cellular RNA was extracted from GM hTERT (lane 2), GM R3E/R6E hTERT (lane 3) and GM L980A/L987AhTERT (lane 4), and a fragment of hTERT mRNA amplified by RT-PCR. Lane 1 shows DNA marker. (B) 1 ug of total cellular extracts from the above mentioned cells were submitted to the TRAP assay to monitor telomerase enzymatic activity. Lane 1 GM hTERT, lane 2: GM R3E/R6E hTERT, lane 3: GM L980A/L987AhTERT, lanes 4 and 5 represent, respectively, negative and positive (HeLa) controls. (C) 5,000 cells were plated/dish and cells were allowed to grow for ~3 weeks, when colonies were stained with INT vital stain and counted. Cell number and size was scored; control cells expressing RasV12 and deficient in p53 were used for the comparisons.

In order to determine if the distinct subcellular localizations of hTERT could contribute differently to tumorigenesis, the present inventor obtained the same cell lines used in the work described above. GM847 cells infected with SV40 and/or overexpressing oncogenic RasV12 were used [Stewart et al. (2002) Proc. Natl. Acad. Sci. USA. 99, 12606-12611]. Control-matched cultures in which GM847 cells (SV40-transformed) expressing oncogenic ras or not oncogenic ras were derived and infected with empty pBabe vector, WT hTERT, nuclear-only hTERT (R3E/R6EhTERT; Santos et al., 2006) or the above described LAhTERT mutant. Telomerase mRNA expression and enzymatic activity were confirmed by RT-PCR and the telomeric repeat amplification protocol (TRAP; FIGS. 1A and B). Next, 5,000 cells were plated in soft agar, and allowed to grow for ~3 weeks, at which time the colonies were stained with INT vital stain and counted. No colonies were observed in cells comprising SV40 and telomerase in the absence of oncogenic ras. Conversely, FIG. 1C shows that GM847 cells comprising SV40/RasV12 produced a large number of colonies, but only when expressing WT or nuclear-only hTERT. Note that while the first have colonies of heterogeneous sizes, the latter showed uniformly larger colonies. Only small colonies were observed in cells expressing LAhTERT. Since these colonies appeared to be essentially morphologically identical to those of control SV40/RasV12 cells, the present inventor concludes that LAhTERT does not support colony growth in soft agar. These data also suggest that the nuclear function of hTERT is involved in its tumorigenic properties.

Expression of LAhTERT causes premature senescence in normal diploid fibroblasts. Because the present inventor and colleagues had previously characterized WT and R3E/R6EhTERT in this cellular background [Santos et al. (2004) Aging Cell. 6, 399-411; Santos et al. (2006) Human Mol. Gen. 15, 1757-1768], the present inventor stably expressed LAhTERT in primary foreskin fibroblasts (NHF) to evaluate its activity in these cells. Unexpectedly, NHF expressing LAhTERT arrested growth, which was accompanied by flattened and enlarged morphology reminiscent of senescent cells. DNA profiles using propidium iodide (PI) and flow cytometry indicated that the cells were blocked in the G1/S transition (FIG. 2A left panel), which is typical (in most cases) of the growth arrest associated with senescence

[Campisi et al. (2007) *Nat Rev Mol Cell Biol.* 9, 729-740]. Analysis of two senescence markers (senescence-associated β galactosidase activity, SA β-gal) and p16$^{INK4a}$ (referred herein as p16) confirmed that NHF expressing L980/L987AhTERT were senescent (FIGS. 2B and 8, respectively).

These results were intriguing given that no additional exogenous stress was imposed upon the cells, and that the phenotype was observed shortly (≦1 week) after viral infections, still during the selection process. However, at least three different simple reasons could account for the senescent phenotype observed.

First, it is possible that NHF underwent replicative senescence during the selection process. In our hands NHF undergo senescence through telomere shortening at about population doubling (PD) 50-60. However, the senescent phenotype was observed irrespective of the PD in which the cells were infected, and as early as PD28. These results were systematically reproduced upon expression of L980/L987AhTERT. Conversely, control NHF (hTERT-negative) infected with empty pBabe vector and submitted to the same selection conditions, at PD42 were still cycling and were also negative for SA β-gal (FIG. 2A middle panel and 2B, respectively). When LAhTERT was introduced into NHF expressing R3E/R6E hTERT (nucTERT), which we showed previously to be immortalized [Santos et al. (2006) *Human Mol. Gen.* 15, 1757-1768] and have rather long telomeres (Herbig, unpublished observation) senescence was still observed (FIG. 2B). Taken together, these data argue against replication-based telomere erosion as the cause for the cell cycle blockade observed.

Second, it had been previously shown that high levels of telomerase in apparently non-stressed cells induce premature senescence [Gorbunova et al. (2003) *J. Biol. Chem.* 278, 7692-7698]. The present inventor then compared levels of hTERT transcript by RT-PCR and of telomerase enzymatic activity by the telomeric repeat amplification protocol (TRAP) in cells carrying WT hTERT (FIG. 2C, lane 1) and cells expressing L980/L987AhTERT (FIG. 2C, lane 2). No significant differences in both parameters were detected between WT control and L980/L987AhTERT cells, suggesting that the cells were not senescing based on the levels of telomerase expression/activity.

LAhTERT modulates cell cycle progression and the sensitivity of cancer cells to oxidative stress. Considering the findings presented above, the present inventor speculated that introduction of the LAhTERT may also impact the growth of cancer cell lines in general. In addition, since mitochondrial hTERT increases both mtDNA damage and apoptosis after $H_2O_2$ [Santos et al. (2006) *Hum Mol. Genet.* 15, 1757-1768], introduction of LAhTERT in cancer cells may increase their sensitivity to genotoxic stress. Note that 90% of all human tumors, including the ones used below, are already telomerase positive [Kim et al. (1994) *Science* 266, 2011-2015].

Figure 2:
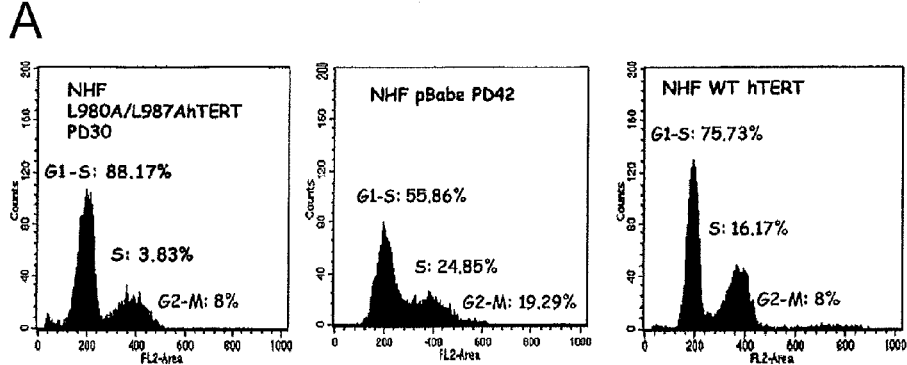
FIG. 2. L980/L987AhTERT cells are blocked in the G1/S transition and have features of cellular senescence. (A) Cell cycle analysis was performed by flow cytometry using propidium iodide (PI). Cells were synchronized by serum starvation overnight. Serum was added to the medium and cells analyzed 8 h after. Data were collected and percentage of cells in each phase of the cell cycle analyzed with CellQuest and ModFit. Results are representative of 3 independent analyses. (B) Senescence associated β-galactosidase was scored using the Cell Signaling Kit. Dark gray cells represent senescent cells. (C) Left panel: RTPCR for a fragment of hTERT and GAPDH; lane 1: WT hTERT and lane 2: L980/L987AhTERT. Right panel shows results from TRAP to detect telomerase enzymatic activity. Lane 1: WT hTERT, lane 2: L980/L987AhTERT, lane 3: positive control (HeLa cells) and lane 4 negative control. IC represents the internal control of the assay.
Figure 2:
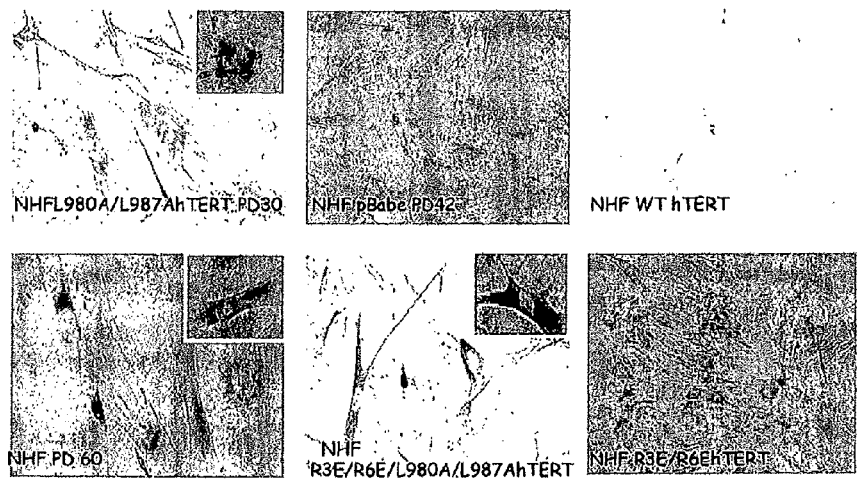
Figure 2:
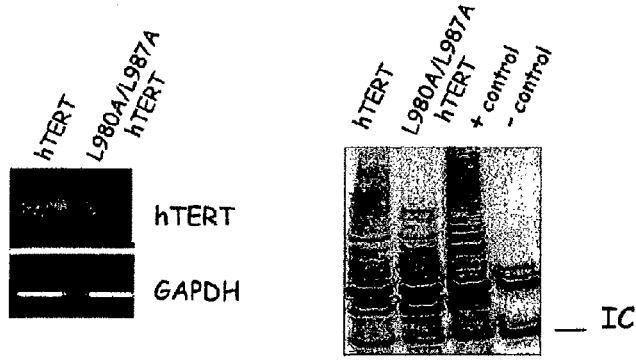

To test this hypothesis, the present inventor stably expressed ectopic L980A/L987AhTERT in SQ20B (squamous cell carcinoma), SCC61 (squamous cell carcinoma) and LNCaP (prostate cancer) cells. As shown in FIG. 2, cell cycle progression was initially monitored by flow cytometry. Cells were synchronized by serum withdrawal overnight, and 8 h after serum addition cells were collected and incubated with RNase and PI. Data are representative of two independent analyses. No differences in cell cycle progression were detected in SCC61 cells in spite of expression of L980A/L987A hTERT. Conversely, both SQ20B as well as LNCaP showed a delay in cell cycle after introduction of ectopic LAhTERT, which was more pronounced in the latter (FIG. 4A). These findings were also confirmed by following cell number for a period of 4 days in dishes in which cells were seeded at the same confluence and by quantifying the incorporation of tritiated thymidine on the DNA. In accordance with the flow cytometry and the cell counting data, a significant decrease in the amount of SQ20B-LAhTERT and LNCaP-LAhTERT in S-phase was observed when compared to the respective controls.

Figure 3:
FIG. 3. Transient expression of L980A/L987AhTERTpCMV alters cell morphology. HeLa cells were transiently transfected with either 20aahTERT-EGFP, in which EGFP is completely mitochondrial [Santos et al. (2004) *Aging Cell.* 6, 399-411] or with L980A/L987AhTERT. The latter were co-transfected with GFP in order to identify cells that had taken up the L980A/L987AhTERT plasmid. Cells were followed up to 72 h after transfection when pictures were taken. Cells were analyzed under a confocal microscope; phase contrast images showed. Both constructs were cloned into the pCMV plasmid (Clontech).

Taken together, these data demonstrate that expression of LAhTERT also delays cell cycle progression of cancer cells. It is also noteworthy that a large proportion of SQ20B cells expressing L980A/L987AhTERT had enlarged morphology, although no senescence associated β-gal was observed (FIG. 4B). This observation is consistent with the results obtained after transient transfection of HeLa cells with the LAhTERT mutant (see FIG. 3).

The present inventor next tested whether the cancer cells carrying L980A/L987AhTERT were also more sensitive to $H_2O_2$ treatment as judged by increased mtDNA damage and apoptosis. To this end, SQ20B and its derivative expressing ectopic LAhTERT were treated with 200 μM of $H_2O_2$ for 60 min. After this period, $H_2O_2$ was removed and cells were allowed to recover for 24 h. Cells were then harvested for DNA extraction and QPCR analysis, or stained with YOPRO-1, an in situ fluorescent probe specific for apoptotic cells [Jerome et al. (2001) *J Immunol.* 167, 3928-3935; Jiang et al. (2005) *Am J Physiol Cell Physiol.* 289, C1295-302; Agrelo et al. (2006) *Proc Natl Acad Sci USA* 103, 8822-8827; Boix-Chornet et al. (2006) *J Biol. Chem.* 281, 13540-13547; Fennell et al. (2006) *J Biomol Screen.* 3, 296-302]. Apoptotic cells were scored under a confocal microscope; total cellular counts (viable plus dead) were also performed.

Figure 5:
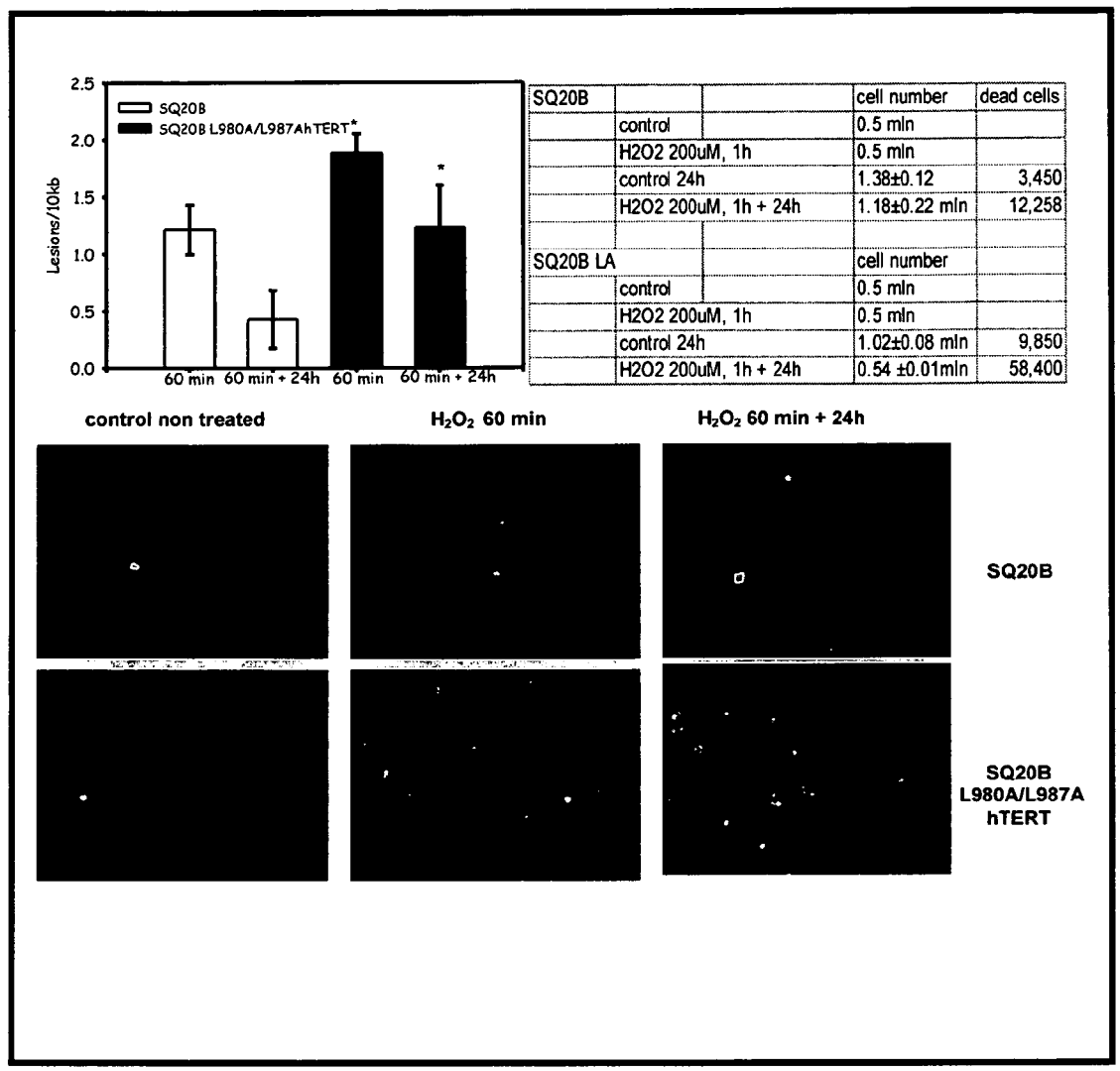
FIG. 5. L980A/L987AhTERT increases the sensitivity of SQ20B cells to hydrogen peroxide treatment. (A) SQ20B wild type or expressing L980A/L987AhTERT were treated with $H_2O_2$ for 60 min, washed and allowed to recover for 24 h. Immediately after the treatment or recovery times, total genomic DNA was isolated and QPCR performed to evaluate mtDNA integrity. Results represent 2 independent experiments; *=p≦0.05. (B) Apoptosis was analyzed based on YOPRO-1 fluorescence immediately after treatment or after the recovery time. The table represents total cell numbers.

As can be seen in FIG. 5A, an enhancement in the levels of mtDNA damage was observed in SQ20B cells carrying the ectopic LAhTERT mutant as compared to WT SQ20B both immediately after treatment and after 24 h of recovery. Associated with this increase in mtDNA damage, the number of apoptotic cells was also higher in SQ20B cells carrying LAhTERT 24 h after the treatments (FIG. 5B). These data were confirmed by immunoblotting to detect caspase-3. Consistent with the augmented apoptosis, more dead cells (gauged by counting the floating cells) were observed in SQ20B L980A/L987A hTERT treated cells. Intriguingly, dead cells were also more abundant in non-treated SQ20B L980A/L987A hTERT as compared to non-treated SQ20B (see Table in FIG. 5).

While SQ20B control and treated, as well as non-treated SQ20B L980A/L987AhTERT, doubled in number at least once in the 24 h period, no change in cell number was observed in treated SQ20B L980A/L987AhTERT. Remarkably, these cells maintained this cell number for 2 additional weeks when they finally started doubling. These results are particularly intriguing considering that SQ20B cells have been shown to be highly resistant to other forms of genotoxic stress such as ionizing radiation [Brachman et al. (1993) *Cancer Res.* 53, 3667-3669].

Collectively, these results suggest that expression of LAhTERT suppresses cell cycle progression of cancer cells. Furthermore, the results also underscore that LAhTERT significantly increases the sensitivity of cancer cells to oxidative stress.

Premature senescence caused by expression of LAhTERT does not require telomerase enzymatic activity. The catalytic activity of telomerase is important for telomere maintenance [Shay et al. (2005) *Carcinogenesis,* 5, 867-874]. To test whether the premature senescence phenotype relied on the enzymatic function of LAhTERT, a catalytically dead LAh- TERT (referred herein as DNLAhTERT, for details on the mutant see Methods and Materials) was generated. At the outset, the mutant was confirmed to be enzymatically inactive by the TRAP; LAhTERT was included as a positive control (FIG. 6A). Subsequently, DNLAhTERT was introduced into NHF and senescence assayed based on SA β-gal. The results presented in FIG. 6B demonstrate that NHF carrying DNLAhTERT also underwent premature senescence, indicating that catalytic activity (at least as judged by TRAP) is not required for the effects of LAhTERT.

Cell cycle arrest induced by LAhTERT involves both p53 and p16. The growth arrest characteristic of senescent cells is established and maintained by two distinct pathways, namely p53 and p16-pRB. While in many cases these pathways interact, in some instances they can work independently of each other to halt cell cycle progression [Campisi et al. (2007) Nat Rev Mol Cell Biol. 9, 729-740]. As indicated herein, the present inventor determined that NHF expressing LAhTERT had elevated p16 levels (FIG. 8 middle bottom panel). This, in turn, led to the question of whether the p53 pathway was also engaged by expression of LAhTERT.

p53 is a transcription factor that coordinates a complex network of proteins evolved to protect cells from malignant transformation. In response to diverse stress factors, p53 induces the expression of different subsets of genes leading to cell cycle arrest, apoptosis, DNA repair, or senescence. For the latter, transactivation of the $p21^{CIP1/WAF}1$ gene (p21 as referred herein) is required [Vogelstein et al. (2000) Nature. 408, 307-310].

To probe the involvement of p53 and its downstream effector p21, both immunoblots and immunofluorescence (IF) studies (FIGS. 7 and 8, respectively) were performed. Initially, whole cell extracts were obtained from control NHF (hTERT-negative, lane 1) and its hTERT derivatives (WT, lane 2; R3E/R6EhTERT, lane 3; and L980/L987AhTERT, lane 4) and evaluated the levels of p53 and p21 protein by immunoblots. The upper panel on FIG. 7A depicts representative data relating to p53 and its quantification relative to loading control (tubulin) is presented below. As can be seen, p53 levels were significantly increased (~5 fold) in NHF carrying LAhTERT when compared to controls; these cells also upregulated p21 (FIG. 7A middle panel). The same results were observed by IF (FIG. 8). Single cell analysis revealed that virtually all cells were positive for p21. Counterstaining of the same cells for p16 showed that most but not all cells that were positive for p21 also upregulated p16 (representative results show in the bottom panel of FIG. 8).

To further test the involvement of p53 for the cell cycle arrest observed, WT or LAhTERT were introduced in fibroblasts infected with the early region of simian virus 40 (SV40ER), which also targets p53 for degradation. Cells were synchronized by serum starvation and DNA content analyzed by flow cytometry using PI 8 h after starvation release. Cell cycle progression resumed to some extent in NHF LAhTERT cells (FIG. 7B middle panel). Note that the levels of cells in S-phase are slightly lower than in controls carrying empty pBabe vector (FIG. 7B left panel) but significantly decreased when compared to cells expressing WT hTERT (FIG. 7B right panel). These data demonstrate that SV40ER transformation allows LAhTERT cells to bypass senescence. Further, they suggest that the senescent phenotype may be only partially dependent on the p53 pathway, likely requiring the concerted action of p53-p21 and p16-pRB.

DNA damage response (DDR) proteins are activated by expression of LAhTERT. Since activation of the p53 and p16-pRB pathways in senescence is commonly the result of DNA damage [Campisi et al. (2007) Nat Rev Mol Cell Biol. 9, 729-740], the above findings prompted an investigation of whether nuclear DNA damage was present in NHF LAhTERT cells. To address this question, activation of proteins involved in DDR was analyzed by immunofluorescence microscopy. Proteins included serine 139 phosphorylated H2AX (gamma-H2AX), activated kinases ataxia telangiectasia mutated (ATM-S1981) and checkpoint 2 (Chk2-T68) as well as phosphorylation of serine 15 (S15) on p53. Controls included NHF (hTERT-negative) at PD28, and NHF expressing either WT hTERT or R3E/R6E hTERT. While very few control or WT hTERT expressing cells displayed visible γH2AX foci (less than 12%), almost all LAhTERT expressing cells displayed at least one visible γH2AX focus (FIG. 8). γH2AX co-localized with active-ATM and -Chk2 kinases demonstrating active double-stranded DNA damage checkpoint signaling [Campisi et al. (2007) supra]. In addition, elevated levels of S15 phosphorylated p53 and p21 were observed in all LAhTERT expressing cells suggesting the senescence growth arrest was mediated, at least in part, by p21. Of note, a few NHF control showed p53S15, which was observed throughout the nucleus. Interestingly, the p53S15 signal in cells carrying L980/L987AhTERT TERT was consistently confined to the nucleolus (FIG. 8; see Discussion).

Nuclear DNA damage in NHF LAhTERT is primarily telomeric. To determine whether the DNA damage foci detected co-localized with telomeres or distributed randomly throughout the chromosomes, telomere dysfunction induced DNA damage foci (TIF) was quantified at a single cell level as done previously [Herbig et al. (2004) Mol Cell. 14, 501-513]. A cell was scored TIF positive when 50% or greater of its DNA damage foci co-localized with telomeric DNA sequences. Consistent with previous observations [Herbig et al. (2004) supra] fewer than 25% of early passage NHF cells were TIF positive (see graph on FIG. 8). Both, WT and R3E/R6EhTERT reduced the levels of TIF positive cells to less than 10%, demonstrating that R3E/R6EhTERT efficiently prevents telomere dysfunction in these cells. In contrast, the majority of DNA damage foci in LAhTERT expressing cells co-localized with telomeric DNA sequences and over 60% of cells were TIF positive (Graph on FIG. 8). These data suggest that cellular senescence in L980/L987AhTERT expressing cells is mediated by telomere dysfunction.

Mitochondria dysfunction and increased ROS are detected in LAhTERT-expressing cells. The nuclear DNA damage detected in NHF carrying LAhTERT is likely the signal for p53 to halt cell cycle progression. However, the question that remains is how expression of LAhTERT causes nuclear DNA damage. Faulty mitochondria can increase basal levels of ROS [Van Houten et al. (2006) DNA Repair, 5, 145-152], and the present inventor previously showed that mitochondrial-derived ROS can damage nuclear DNA [Karthikeyan et al. (2003) Hum Mol Genet. 24, 3331-3342; Stuart et al. (2006) Hum Mol. Genet. 15, 363-374]. The present inventor hypothesized that expression of LAhTERT causes mitochondrial dysfunction such that it raises the basal levels of ROS, which in turn damage nuclear DNA. To test these premises, ATP production and mitochondrial morphology were monitored by electron microscopy (EM) as well as basal levels of mitochondrial ROS generation.

Since mitochondria are the main site of ATP production, total cellular ATP is a surrogate of proper mitochondrial function. ATP levels were measured in NHF (hTERT-negative) and the hTERT derivatives by luminescence (see Experimental Procedures). As depicted in FIG. 9A, a significant drop in ATP levels is observed in NHF LAhTERT, which is independent of the PD that cells were assayed.

Mitochondrial impairment is often accompanied by changes in organellar morphology such as swelling, loss of cristae and the appearance of megamitochondria [Kim et al. (2007) *Arch Biochem Biophys.* 462, 245-253]. Corroborating the ATP data, analysis of mitochondrial ultrastructure by EM showed that expression of LAhTERT caused a dramatic change in organellar morphology with loss of cristae, intra-mitochondrial inclusions and a significant decrease in mitochondrial size (FIG. 9B). No worm-shaped mitochondria as observed in NHF control and in cells expressing WT or R3E/R6EhTERT were detected (FIG. 9B).

The EM images suggest a decrease in mitochondrial content in LAhTERT cells. It is generally accepted that mtDNA copy number and overall mitochondrial biogenesis are coordinately regulated [Eaton et al. (2007) *J Clin Invest.* 117: 2723-2734]. Thus, the present inventor next asked whether mtDNA content was decreased in cells carrying LAhTERT. Because of the premature senescence, it was not possible to obtain enough NHF LAhTERT for mtDNA analysis. Since SV40-transformation allowed LAhTERT cells to bypass senescence (FIG. 7B), mtDNA copy number in those cells was analyzed and interpreted as representative data. A decrease in mtDNA content was indeed identified in SV40-transformed LAhTERT cells (FIG. 9C). These results were also confirmed in cancer cells infected with the mutant protein. Taken together, the ATP, EM and mtDNA content data strongly support the idea that expression of LAhTERT has a negative impact on mitochondria.

Having identified that the mitochondria of NHF carrying LahTERT were dysfunctional, basal levels of ROS were measured in the cells. For that purpose, Mitosox Red™, a dye specific for the detection of mitochondrial superoxide anion ($O_2^-$) was used. See The Handbook, A Guide to Fluorescent Probes and Labeling Technologies, available online at Invitrogen.com. For these experiments, Mitosox fluorescence was evaluated at a single cell level by confocal microscopy. NHF, derivatives carrying WT, R3E/R6EhTERT, LAhTERT or DNLAhTERT were assayed; old NHF (at PD51) were also included since senescent cells reportedly produce high levels of $O_2^-$ [Passos et al. (2007) *PLoS Biol.* 5, e110]. Approximately 50 cells per coverslip and 6 coverslips per cell type were analyzed. The fluorescence intensity was quantified using Image J software; background fluorescence was also subtracted. Statistical significance was calculated using ANOVA.

As reported previously [Passos et al. (2007) *PLoS Biol.* 5, e110], senescent NHF showed a significant increase in the levels of $O_2^-$ when compared to young controls (FIG. 9D compare gray to open bar). However, the increase in Mitosox fluorescence was even higher in NHF LAhTERT or DNLAhTERT, which was statistically different when compared to both young and old NHF (FIG. 9D compare dashed bars to open and gray bars). These results demonstrate that expression of LAhTERT significantly increases the mitochondrial production of ROS, which is not the result of the senescent phenotype but likely due to the high degree of mitochondrial dysfunction in these cells. Further, the data corroborate the findings presented in FIG. 6 that catalytic activity is not required for the effects of LAhTERT. As reported by others [Ahmed et al. (2008) *J Cell Sci.* 121, 1046-1053], cells expressing WT hTERT (black bar) showed a slight but significant decrease in Mitosox fluorescence when compared to young NHF (open bar). A decrease in fluorescence was observed in cells carrying R3E/R6EhTERT, which was significantly different from that of NHF at PD51 (FIG. 9D). The involvement of ROS was confirmed by incubating the LAhTERT cells at the time of viral infection with N-acetyl cysteine (NAC), a precursor of glutathione synthesis shown to significantly increase the intracellular pool of thiol-antioxidants [Wang et al. (1998) *J Biol. Chem.* 273, 33027-33034]. In such cases, no cell cycle blockade or SA β-gal activity were detected. Altogether, these data demonstrate that mitochondrial dysfunction and mitochondrial-derived ROS are responsible for the premature senescence associated with expression of LAhTERT.

Discussion

These results demonstrate that expression of LAhTERT does not support colony growth in soft agar, and that it dramatically delays cell growth in normal human cells while slowing down cell cycle progression of cancer cells. In addition, the present inventor has shown that LAhTERT expressed either transiently or stably alters cell morphology. Finally, data are presented that demonstrate that expression of LAhTERT in cancer cell lines increases mtDNA damage and an associated apoptotic cell death following oxidative stress.

It had been shown by Stewart and co-workers [(2002) *Proc. Natl. Acad. Sci. USA.* 99, 12606-12611] that telomerase contributes to tumorigenesis independently from its function in telomere elongation. The authors used cell lines that maintain telomeres independent of telomerase (ALT cells) in combination with p53 deficiency (through infection of cells with small and large T antigens of the SV40 virus) and by overexpressing oncogenic RasV12. In this scenario, they demonstrated that hTERT is required for the formation of colonies in soft agar. The same held true when tumor formation in nude mice was assayed. The use of a telomerase version that is catalytically active, but unable to elongate telomeres (hTERT-HA) allowed the authors to conclude that the effects of telomerase in tumorigenesis did not relate to its telomere function as this telomere-impaired enzyme still supported colony and tumor formation in both assays described above [Stewart et al. (2002) *Proc. Natl. Acad. Sci. USA.* 99, 12606-12611].

As shown herein, no differences in the pattern of colony formation in soft agar were observed when the same cells used above expressed LAhTERT. In fact, only when cells expressed hTERT in the nucleus were a significant number of colonies (with enlarged size as well) observed. These findings suggest that the nuclear localization of hTERT contributes to the function of telomerase in tumorigenesis, which may only require its telomeric activity.

Further support for this conclusion derives from work recently published by Sun and co-workers (Cancer Res. 2005, 15:6512-5). Contrary to Stewart's findings, these authors demonstrate that ALT-SV40-immortalized fibroblast cell lines required only oncogenic RasV12G to be converted to a fully tumorigenic state. When cells were implanted beneath the kidney capsule of immunodeficient mice, they invaded the kidney and neighboring organs and metastasized to the lungs. Ras(V12G)-expressing ALT cells remained completely telomerase negative. Introduction of hTERT conferred strong telomerase activity, but did not appreciably change the malignant properties of the cells. However, when cells were tested by subcutaneous injection, RasV12G-transduced ALT cells did not form tumors, and in this site, hTERT was required for tumorigenicity. These data show that when the subcutaneous injection method is used as an assay for tumorigenicity, hTERT may be artifactually scored as an oncogene; the subrenal capsule assay shows that ALT, as a telomere maintenance mechanism, is equivalent to hTERT in neoplastic transformation of human cells by oncogenes (Cancer Res. 2005, 15:6512-5).

The results presented herein also demonstrate that expression of LAhTERT causes significant mitochondrial dysfunction with an associated elevation in the basal levels of ROS (See FIG. 9). These species damage the nuclear DNA primarily at telomeres, triggering DDR genes and premature senescence (See FIG. 8 and FIG. 2). The cell cycle blockade is dependent on both p53, and Rb (See FIG. 7 and FIG. 8). Compelling evidence is also presented herein demonstrating that the cell cycle effects of LAhTERT are independent of telomerase's catalytic activity (See FIG. 6).

The present inventor further shows that LAhTERT cells have highly dysfunctional mitochondria, with a significant decrease in ATP levels, altered mitochondrial ultrastructure, decreased mtDNA content and high production of ROS (See FIG. 9). These data are in accordance with previous work demonstrating that hTERT promotes mitochondrial damage [Santos et al. (2004) *Aging Cell.* 6, 399-411; Santos et al. (2006) *Human Mol Gen.* 15, 1757-1768].

The idea of mitochondrial dysfunction in cellular senescence is not a new concept [Passos et al. (2007) *PLoS Biol.* 5, e110; Hutter et al. 2004 *Biochem J.* 380, 919-928]. The finding that LAhTERT expression, however, causes premature senescence is surprising. Herein, the present inventor demonstrates a direct link between expression of LAhTERT and cellular senescence and mitochondrial-ROS driven telomere damage. The present inventor not only shows that expression of LAhTERT activates DDR genes, which respond to nuclear DNA damage, but also that the damage is primarily localized at telomeres. Indeed, ~60% of all nuclear damage in LAhTERT cells is telomeric (See FIG. 8). This number may be underestimated given that LAhTERT cells have rather short telomeres, raising the possibility that some telomeres were too short to be detected with the telomeric probe.

The present inventor and colleagues previously demonstrated that on average ~75% of nuclear DNA damage is localized at telomeres during replicative senescence [Herbig et al. (2004) *Mol Cell.* 14, 501-513]. Based on the time frame for the senescence induced by LAhTERT (less than 7 days), it is unlikely that the TIF detected result from replication-based telomere shortening. It is more probable that the TIF associated with expression of LAhTERT reflect oxidation of bases at telomeres resulting from dysfunctional mitochondria (See FIG. 9). Oxidative damage has been associated with telomere uncapping [von Zglinicki. (2002) *Trends Biochem Sci.,* 27, 339-344; Balaban et al. (2005) *Cell* 120, 483-495] and telomeric sequences are a preferential target of oxidative stress [Henle et al. (1999) *J. Biol. Chem.* 274, 962-971].

Telomere-binding proteins are unable to bind to oxidized telomeric traits, ultimately triggering a p53-dependent cell cycle arrest [von Zglinicki. (2002) *Trends Biochem Sci.,* 27, 339-344]. The present results suggest that LAhTERT driven premature senescence is at least partially dependent on p53. This conclusion is based on the fact that when p53 is targeted for degradation, LAhTERT cells resumed growth (see FIG. 7B). Note that SV40ER also targets the pRB pathway [Herbig et al. (2006) *Mech Ageing Dev.* 127, 16-24]. The concerted action of p53 and RB for the establishment and maintenance of the senescent phenotype is well recognized (for recent reviews see Campisi et al. (2007) *Nat Rev Mol Cell Biol.* 9, 729-740 and Herbig et al. (2006) *Mech Ageing Dev.* 127, 16-24). Given that NHF LAhTERT also upregulate p16, it is possible that both of these pathways must be active to cause LAhTERT-dependent complete cell cycle arrest. In agreement with this hypothesis, introduction of LAhTERT in cancer cell lines deficient in either p53 or p16 cause a significant delay in cell cycle progression but no cell cycle blockade. One cannot discard the involvement of additional pathways, but further studies are required to bring light onto this issue.

Curiously, the phosphorylated form of p53 (p53S15) consistently localized to the nucleolus in LAhTERT cells (See representative data in FIG. 8). Few reports deal with the nucleolar localization of p53 but, in general, abnormal localization of p53 is thought as a means to inactivate p53 function [Karni-Schmidt et al. (2007) *Oncogene* 26(26):3878-91; Klibanov et al. (2001) *J Cell Sci.* 114, 1867-1873].

Biological Implications.

Telomerase is expressed during development, in highly proliferative somatic cells in the adult and in the majority of cancers. In the past years, telomerase has become a promising target for cancer treatment since most normal cells are telomerase negative and therefore drugs aiming at this enzyme are fairly selective to cancer cells (even though side effects are still observed in stem cells and highly proliferative cells in the adult). Further, cancer diagnostic and even prognostic applications for telomerase have been proposed and intensively investigated [Kelland. (2001) *Lancet Oncol.* 2, 95-102].

Several approaches have been developed to block the activity of telomerase holoenzyme in cancer cells such as antisense oligonucleotides against either hTERT or hTR [Herbert et al. (1999) *Proc Natl Acad Sci USA.* 96, 14276-14281; Kraemer et al. (2003) *Clin Cancer Res.* 9, 3794-3800; Li et al. (2005) *J Biol. Chem.* 280, 23709-23717; Nakamura et al. (2005) *Hum Gene Ther.* 7, 859-868], inactive variants of hTERT that act as dominant negatives [Hahn et al. (1999) *Nat Med.* 10, 1164-1170; Zhang et al. (1999) *Genes Dev.* 13, 2388-2399], small chemical compounds against hTERT [Damm et al. (2001) *EMBO J.* 24, 6958-6968; Corey. (2002) *Oncogene.* 21, 631-617; Ward et al. (2005) *Mol Pharmacol.* 68, 779-786; Gellert et al. (2006) *Breast Cancer Res Treat.* 96, 73-81], and G-quadruplex-stabilizing agents that bind the telomeric ends and block telomerase access and elongation [Hurley et al. (2000) *Pharmacol Ther.* 85, 141-58; Riou et al. (2002) *Proc Natl Acad Sci USA.* 99, 2672-2667; Burger et al. (2005) *Cancer Res.* 65, 1489-1496]. In all cases, direct or indirect telomerase inhibition results in the inability of the cells to maintain telomeres and ultimately such cells arrest growth or die. However, the main problem of these approaches is that several weeks/months are required for the effects, which rely on extensive telomere shortening [Cerone et al. (2006) *Mol Cancer Ther.* 7, 1669-1675]. Nonetheless, telomerase inhibitors are currently in clinical trials [Kelland. (2001) *Lancet Oncol.* 2, 95-102].

The data presented herein suggest that elimination of telomerase as a whole from the cells may not be the most effective or best strategy to counteract tumor growth. In fact, based on the results presented herein, expression of LAhTERT in cancer cells is anticipated to be useful as a therapeutic strategy for slowing down tumor growth and increasing tumor sensitivity to genotoxic agents. Importantly, these effects are observed in a few days after introduction of this altered protein. Therefore, modulation of telomerase activity following expression of LAhTERT represents a promising means to efficiently tackle anti-tumor therapy.

The data presented herein and taken together with our previous findings [Santos et al. (2004) *Aging Cell.* 6, 399-411; Santos et al. (2006) *Human Mol Gen.* 15, 1757-1768] suggest a role for hTERT in cell cycle decisions. The choice between senescence and apoptosis likely depends on the mitochondrial oxidative environment, and on the initial amount of damage present in the organelle. In either case, while the effects of hTERT seem detrimental to mitochondria, they are beneficial to the cell/tissue as a whole. This is consistent with a role for hTERT in development when integrity of the cells is key to normal tissue and organismal development. It seems highly beneficial that the same protein that gives indefinite proliferative potential to stem cells also has a role in mitochondrial quality control. Telomerase is also overexpressed in cancers and ironically many reports show that inhibition of its function increases apoptosis in these cells (58-62). These observations raise the possibility that mitochondrial functions of endogenous hTERT are either abolished or impaired in tumor cells. In support of this hypothesis, expression of LAhTERT, which exhibits altered cellular localization relative to hTERT, in two different cancer cell lines not only causes a dramatic delay in cell cycle progression but significantly sensitizes the cells to $H_2O_2$ (See FIG. 4 and FIG. 5). Thus manipulation of TERT's subcellular localization represents a novel and promising strategy to counteract tumor growth.

The nucleic and amino acid sequences of wild type hTERT and the L980A/L987AhTERT mutant are presented below:

```
DNA sequence of wild type hTERT.
atgccgcgcgctccccgctgccgagccgtgcgctccctgctgcgcagcca ctaccgcgaggtgctgccgctggccacgttcgtgcggcgcctggggcccc agggctggcggctggtgcagcgcggggacccggcggctttccgcgcgctg gtggcccagtgcctggtgtgcgtgccctgggacgcacggccgccccccgc cgccccctccttccgccaggtgtcctgcctgaaggagctggtggcccgag tgctgcagaggctgtgcgagcgcggcgcgaagaacgtgctggccttcggc ttcgcgctgctggacggggcccgcgggggccccccgaggccttcaccac cagcgtgcgcagctacctgcccaacacggtgaccgacgcactgcggggga gcggggcgtgggggctgctgctgcgccgcgtgggcgacgacgtgctggtt cacctgctggcacgctgcgcgctctttgtgctggtggctcccagctgcgc ctaccaggtgtgcgggccgccgctgtaccagctcggcgctgccactcagg cccggcccccgccacacgctagtggacccccgaaggcgtctgggatgcgaa cgggcctggaaccatagcgtcagggaggccggggtccccctgggcctgcc agccccgggtgcgaggaggcgcgggggcagtgccagccgaagtctgccgt tgcccaagaggcccaggcgtggcgctgcccctgagccggagcggacgccc gttgggcagggtcctgggcccacccgggcaggacgcgtggaccgagtga ccgtggtttctgtgtggtgtcacctgccagacccgccgaagaagccacct ctttggagggtgcgctctctggcacgcgccactcccacccatccgtgggc cgccagcaccacgcgggccccccatccacatcgcggccaccacgtccctg ggacacgccttgtccccggtgtacgccgagaccaagcacttcctctact cctcaggcgacaaggagcagctgcggccctccttcctactcagctctctg aggcccagcctgactggcgctcggaggctcgtggagaccatctttctggg ttccaggccctggatgccagggactccccgcaggttgccccgcctgcccc agcgctactggcaaatgcggcccctgtttctggagctgcttgggaaccac gcgcagtgcccctacggggtgctcctcaagacgcactgcccgctgcgagc tgcggtcacccagcagccggtgtctgtgcccgggagaagcccagggct ctgtggcggcccccgaggaggaggacacagacccccgtcgcctggtgcag ctgtccgccagcacagcagccctggcaggtgtacggcttcgtgcgggc ctgcctgcgccggctggtgccccaggcctctggggctccaggcacaacg aacgccgcttcctcaggaacaccaagaagttcatctccctggggaagcat
```

```
gccaagctctcgctgcaggagctgacgtggaagatgagcgtgcgggactg cgcttggctgcgcaggagcccaggggttggctgtgttccggccgcagagc accgtctgcgtgaggagatcctggccaagttcctgcactggctgatgagt gtgtacgtcgtcgagctgctcaggtctttcttttatgtcacggagaccac gtttcaaaagaacaggctcttttctaccggaagagtgtctggagcaagt tgcaaagcattggaatcagacagcacttgaagagggtgcagctgcgggag ctgtcggaagcagaggtcaggcagcatcgggaagccaggcccgccctgct gacgtccagactccgcttcatccccaagcctgacgggctgcggccgattg tgaacatggactacgtcgtgggagccagaacgttccgcagagaaaagagg gccgagcgtctcacctcgagggtgaaggcactgttcagcgtgctcaacta cgagcgggcgcggcgccccggcctcctgggcgcctctgtgctgggcctgg acgatatccacagggcctggcgcaccttcgtgctgcgtgtgcgggcccag gacccgccgcctgagctgtactttgtcaaggtggatgtgacgggcgcgta cgacaccatccccaggacaggctcacggaggtcatcgccagcatcatca aaccccagaacacgtactgcgtgcgtcggtatgccgtggtccagaaggcc gcccatgggcacgtccgcaaggccttcaagagccacgtctctaccttgac agacctccagccgtacatgcgacagttcgtggctcacctgcaggagacca gcccgctgagggatgccgtcgtcatcgagcagagctcctccctgaatgag gccagcagtggcctcttcgacgtcttcctacgcttcatgtgccaccacgc cgtgcgcatcaggggcaagtcctacgtccagtgccaggggatcccgcagg gctccatcctctccacgctgctctgcagcctgtgctacggcgacatggag aacaagctgtttgcggggattcggcgggacgggctgctcctgcgctttgt ggatgatttcttgttggtgacacctcacctcacccacgcgaaaacctttcc tcaggaccctggtccgaggtgtccctgagtatggctgcgtggtgaacttg cggaagacagtggtgaacttccctgtagaagacgaggccctgggtggcac ggcttttgttcagatgccggcccacggcctattccctggtgcggcctgc tgctggataccccgaccctggaggtgcagagcgactactccagctatgcc cggacctccatcagagccagtctcaccttcaaccgcggcttcaaggctgg gaggaacatgcgtcgcaaactcttggggtcttgcg*ct*gaagtgtcaca gcctgttt*ctg*gatttgcaggtgaacagcctccagacggtgtgcaccaac atctacaagatcctcctgctgcaggcgtacaggtttcacgcatgtgtgct gcagctcccatttcatcagcaagtttggaagaaccccacattttttcctgc gcgtcatctctgacacggcctccctctgctactccatcctgaaagccaag aacgcagggatgtcgctgggggccaagggcgccgccggccctctgccctc cgaggccgtgcagtggctgtgccaccaagcattcctgctcaagctgactc gacaccgtgtcacctacgtgccactcctggggtcactcaggacagcccag acgcagctgagtcggaagctcccggggacgacgctgactgccctggaggc cgcagccaacccggcactgccctcagacttcaagaccatcctggac Amino acid sequence of wild type hTERT
MPRAPRCRAVRSLLRSHYREVLPLATFVRRLGPQGWRLVQRGDPAAFRAL

VAQCLVCVPWDARPPPAAPSFRQVSCLKELVARVLQRLCERGAKNVLAFG
```

FALLDGARGGPPEAFTTSVRSYLPNTVTDALRGSGAWGLLLRRVGDDVLV
HLLARCALFVLVAPSCAYQVCGPPLYQLGAATQARPPPHASGPRRRLGCE
RAWNHSVREAGVPLGLPAPGARRRGGSASRSLPLPKRPRRGAAPEPERTP
VGQGSWAHPGRTRGPSDRGFCVVSPARPAEEATSLEGALSGTRHSHPSVG
RQHHAGPPSTSRPPRPWDTPCPPVYEATKHFLYSSGDKEQLRPSFLLSSL
RPSLTGARRLVETIFLGSRPWMPGTPRRLPRLPQRYWQMRPLFLELLGNH
AQCPYGVLLKTHCPLRAAVTPAAGVCAREKPQGSVAAPEEEDTDPRRLVQ
LLRQHSSPWQVYGFVRACLRRLVPPGLWGSRHNERRFLRNTKKFISLGKH
AKLSLQELTWKMSVRDCAWLRRSPGVGCVPAAEHRLREEILAKFLHWLMS
VYVVELLRSFFYVTETTFQKNRLFFYRKSVWSKLQSIGIRQHLKRVQLRE
LSEAEVRQHREARPALLTSRLRFIPKPDGLRPIVNMDYVVGARTFRREKR
AERLTSRVKALFSVLNYERARRPGLLGASVLGLDDIHRAWRTFVLRVRAQ
DPPPELYFVKVDVTGAYDTIPQDRLTEVIASIIKPQNTYCVRRYAVVQKA
AHGHVRKAFKSHVSTLTDLQPYMRQFVAHLQETSPLRDAVVIEQSSSLNE
ASSGLFDVFLRFMCHHAVRIRGKSYVQCQGIPQGSILSTLLCSLCYGDME
NKLFAGIRRDGLLLRLVDDFLLVTPHLTHAKTFLRTLVRGVPEYGCVVNL
RKTVVNFPVEDEALGGTAFVQMPAHGLFPWCGLLLDTRTLEVQSDYSSYA
RTSIRASLTFNRGFKAGRNMRRKLFGVLRLKCHSLFLDLQVNSLQTVCTN
IYKILLLQAYRFHACVLQLPFHQQVWKNPTFFLRVISDTASLCYSILKAK
NAGMSLGAKGAAGPLPSEAVQWLCHQAFLLKLTRHRVTYVPLLGSLRTAQ
TQLSRKLPGTTLTALEAAANPALPSDFKTILD

DNA sequence of the L980A/L987AhTERT mutant
atgccgcgcgctccccgctgccgagccgtgcgctccctgctgcgcagcca
ctaccgcgaggtgctgccgctggccacgttcgtgcggcgcctggggcccc
agggctggcggctggtgcagcgcggggacccggcggctttccgcgcgctg
gtggcccagtgcctggtgtgcgtgccctgggacgcacggccgccccccgc
cgcccctccttccgccaggtgtcctgcctgaaggagctggtggcccgag
tgctgcagaggctgtgcgagcgcggcgcgaagaacgtgctggccttcggc
ttcgcgctgctggacggggcccgcggggccccccccgaggccttcaccac
cagcgtgcgcagctacctgcccaacacggtgaccgacgcactgcggggga
gcggggcgtgggggctgctgctgcgccgcgtgggcgacgacgtgctggtt
cacctgctggcacgctgcgcgctctttgtgctggtggctcccagctgcgc
ctaccaggtgtgcgggccgccgctgtaccagctcggcgctgccactcagg
cccggcccccgccacacgctagtggaccccgaaggcgtctgggatgcgaa
cgggcctggaaccatagcgtcaggaggccggggtcccctgggcctgcc
agccccgggtgcgaggaggcgcggggcagtgccagccgaagtctgccgt
tgcccaagaggcccaggcgtggcgctgccccctgagccggagcggacgccc
gttgggcaggggtcctgggcccacccgggcaggacgcgtggaccgagtga
ccgtggtttctgtgtggtgtcacctgccagacccgccgaagaagccacct
ctttggagggtgcgctctctggcacgcgccactcccacccatccgtgggc
cgccagcaccacgcgggccccccatccacatcgcggccaccacgtccctg ggacacgccttgtcccccggtgtacgccgagaccaagcacttcctctact
cctcaggcgacaaggagcagctgcggcccctcttcctactcagctctctg
aggcccagcctgactggcgctcggaggctcgtggagaccatcttctgggg
ttccaggccctggatgccaggactccccgcaggttgccccgcctgcccc
agcgctactggcaaatgcggcccctgtttctggagctgcttgggaaccac
gcgcagtgccctacggggtgctcctcaagacgcactgcccgctgcgagc
tgcggtcaccccagcagccggtgtctgtgcccgggagaagcccagggct
ctgtggcggccccgaggaggaggacacagaccccgtcgcctggtgcag
ctgctccgccagcacagcagccctggcaggtgtacggcttcgtgcgggc
ctgcctgcgccggctggtgccccaggcctctggggctccaggcacaacg
aacgccgcttcctcaggaacaccaagaagttcatctccctggggaagcat
gccaagctctcgctgcaggagctgacgtggaagatgagcgtgcgggactg
cgcttggctgcgcaggagcccaggggttggctgtgttccggccgcagagc
accgtctgcgtgaggagatcctggccaagttcctgcactggctgatgagt
gtgtacgtcgtcgagctgctcaggtctttcttttatgtcacggagaccac
gtttcaaaagaacaggctctttttctaccggaagagtgtctggagcaagt
tgcaaagcattggaatcagacagcacttgaagagggtgcagctgcgggag
ctgtcggaagcagaggtcaggcagcatcgggaagccaggcccgccctgct
gacgtccagactccgcttcatccccaagcctgacgggctgcggccgattg
tgaacatggactacgtcgtgggagccagaacgttccgcagagaaaagagg
gccgagcgtctcacctcgagggtgaaggcactgttcagcgtgctcaacta
cgagcgggcgcggcgccccggcctcctgggcgcctctgtgctgggcctgg
acgatatccacagggcctggcgcaccttcgtgctgcgtgtgcgggcccag
gacccgccgcctgagctgtactttgtcaaggtggatgtgacgggcgcgta
cgacaccatccccaggacaggctcacggaggtcatcgccagcatcatca
aacccagaacacgtactgcgtgcgtcggtatgccgtggtccagaaggcc
gcccatgggcacgtccgcaaggccttcaagagccacgtctctaccttgac
agacctccagccgtacatgcgacagttcgtggctcacctgcaggagacca
gcccgctgagggatgccgtcgtcatcgagcagagctcctccctgaatgag
gccagcagtggcctcttcgacgtcttcctacgcttcatgtgccaccacgc
cgtgcgcatcaggggcaagtcctacgtccagtgccagggatcccgcagg
gctccatcctctccacgctgctctgcagcctgtgctacggcgacatggag
aacaagctgtttgcggggattcggcgggacgggctgctcctgcgtttggt
ggatgatttcttgttggtgacacctcacctcacccacgcgaaaaccttcc
tcaggaccctggtccgaggtgtccctgagtatggctgcgtggtgaacttg
cggaagacagtggtgaacttccctgtagaagacgaggccctgggtggcac
ggcttttgttcagatgccggcccacggccattccctggtgcggcctgc
tgctggataccggaccctggaggtgcagagcgactactccagctatgcc
cggacctccatcagagccagtctcaccttcaaccgcggcttcaaggctgg
gaggaacatgcgtcgcaaactcttttgggtcttgcgg<u>gcg</u>aagtgtcaca -continued
```
gcctgtttgcggatttgcaggtgaacagcctccagacggtgtgcaccaac
atctacaagatcctcctgctgcaggcgtacaggtttcacgcatgtgtgct
gcagctcccatttcatcagcaagtttggaagaaccccacatttttcctgc
gcgtcatctctgacacggcctccctctgctactccatcctgaaagccaag
aacgcagggatgtcgctgggggccaagggcgccgccggccctctgccctc
cgaggccgtgcagtggctgtgccaccaagcattcctgctcaagctgactc
gacaccgtgtcacctacgtgccactcctggggtcactcaggacagcccag
acgcagctgagtcggaagctcccggggacgacgctgactgcctggaggc
cgcagccaacccggcactgccctcagacttcaagaccatcctggacga
```

Amino acid sequence of L980A/L987AhTERT - mutation
is shown in bold and underlined
```
MPRAPRCRAVRSLLRSHYREVLPLATFVRRLGPQGWRLVQRGDPAAFRAL
VAQCLVCVPWDARPPPAAPSFRQVSCLKELVARVLQRLCERGAKNVLAFG
FALLDGARGGPPEAFTTSVRSYLPNTVTDALRGSGAWGLLLRRVGDDVLV
HLLARCALFVLVAPSCAYQVCGPPLYQLGAATQARPPPHASGPRRRLGCE
RAWNHSVREAGVPLGLPAPGARRRGGSASRSLPLPKRPRRGAAPEPERTP
VGQGSWAHPGRTRGPSDRGFCVVSPARPAEEATSLEGALSGTRHSHPSVG
RQHHAGPPSTSRPPRPWDTPCPPVYAETKHFLYSSGDKEQLRPSFLLSSL
RPSLTGARRLVETIFLGSRPWMPGTPRRLPRLPQRYWQMRPLFLELLGNH
AQCPYGVLLKTHCPLRAAVTPAAGVCAREKPQGSVAAPEEEDTDPRRLVQ
LLRQHSSPWQVYGFVRACLRRLVPPGLWGSRHNERRFLRNTKKFISLGKH
AKLSLQELTWKMSVRDCAWLRRSPGVGCVPAAEHRLREEILAKFLHWLMS
VYVVELLRSFFYVTETTFQKNRLFFYRKSVWSKLQSIGIRQHLKRVQLRE
LSEAEVRQHREARPALLTSRLRFIPKPDGLRPIVNMDYVVGARTFRREKR
AERLTSRVKALFSVLNYERARRPGLLGASVLGLDDIHRAWRTFVLRVRAQ
DPPPELYFVKVDVTGAYDTIPQDRLTEVIASIIKPQNTYCVRRYAVVQKA
AHGHVRKAFKSHVSTLTDLQPYMRQFVAHLQETSPLRDAVVIEQSSSLNE
ASSGLFDVFLRFMCHHAVRIRGKSYVQCQGIPQGSILSTLLCSLCYGDME
NKLFAGIRRDGLLLRLVDDFLLVTPHLTHAKTFLRTLVRGVPEYGCVVNL
RKTVVNFPVEDEALGGTAFVQMPAHGLFPWCGLLLDTRTLEVQSDYSSYA
RTSIRASLTFNRGFKAGRNMRRKLFGVLRAKCHSLFADLQVNSLQTVCTN
IYKILLLQAYRFHACVLQLPFHQQVWKNPTFFLRVISDTASLCYSILKAK
NAGMSLGAKGAAGPLPSEAVQWLCHQAFLLKLTRHRVTYVPLLGSLRTAQ
TQLSRKLPGTTLTALEAAANPALPSDFKTILD
```

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated polypeptide comprising SEQ ID NO: 2, wherein said isolated polypeptide effects a delay in cell cycle progression and increases sensitivity of cells to mitochondrial DNA damage or apoptosis induced by an oxidative stressor.

2. An isolated antibody immunologically specific for the isolated polypeptide comprising SEQ ID NO:2.

3. The antibody of claim 2, wherein said antibody is a polyclonal antibody.

4. The antibody of claim 2, wherein said antibody is a monoclonal antibody.

* * * * *

SEQUENCE LISTING

<160> NUMBER OF SEQ ID NOS: 8

<210> SEQ ID NO 1
<211> LENGTH: 3398
<212> TYPE: DNA
<213> ORGANISM: Homo sapiens

<400> SEQUENCE: 1

```
atgccgcgcg ctccccgctg ccgagccgtg cgctccctgc tgcgcagcca ctaccgcgag      60
gtgctgccgc tggccacgtt cgtgcggcgc ctggggcccc agggctggcg gctggtgcag     120
cgcggggacc cggcggcttt ccgcgcgctg gtggcccagt gcctggtgtg cgtgccctgg     180
gacgcacggc cgccccccgc cgcccccctcc ttccgccagg tgtcctgcct gaaggagctg     240
gtggcccgag tgctgcagag gctgtgcgag cgcggcgcga agaacgtgct ggccttcggc     300
ttcgcgctgc tggacggggc ccgcggggc cccccgagg ccttcaccac cagcgtgcgc      360
agctacctgc ccaacacggt gaccgacgca ctgcggggga gcggggcgtg ggggctgctg     420
ctgcgccgcg tgggcgacga cgtgctggtt cacctgctgg cacgctgcgc gctctttgtg     480
ctggtggctc ccagctgcgc ctaccaggtg tgcggccgc cgctgtacca gctcggcgct     540
gccactcagg cccggccccc gccacacgct agtggacccc gaaggcgtct gggatgcgaa     600
cgggcctgga accatagcgt cagggaggcc gggtccccc tgggcctgcc agccccgggt     660
gcgaggaggc gcggggcag tgccagccga agtctgccgt tgcccaagag gcccaggcgt     720
ggcgctgccc tgagccgga gcggacgccc gttgggcagg gtcctgggc ccacccgggc     780 aggacgcgtg gaccgagtga ccgtggtttc tgtgtggtgt cacctgccag acccgccgaa     840
```

```
gaagccacct ctttggaggg tgcgctctct ggcacgcgcc actcccaccc atccgtgggc   900
cgccagcacc acgcgggccc cccatccaca tcgcggccac cacgtccctg ggacacgcct   960
tgtcccccgg tgtacgccga gaccaagcac ttcctctact cctcaggcga caaggagcag  1020
ctgcggccct ccttcctact cagctctctg aggcccagcc tgactggcgc tcggaggctc  1080
gtggagacca tctttctggg ttccaggccc tggatgccag ggactccccg caggttgccc  1140
cgcctgccc agcgctactg gcaaatgcgg cccctgtttc tggagctgct tgggaaccac  1200
gcgcagtgcc cctacggggt gctcctcaag acgcactgcc cgctgcgagc tgcggtcacc  1260
ccagcagccg tgtctgtgc ccgggagaag ccccagggct ctgtggcggc ccccgaggag  1320
gaggacacag accccccgtcg cctggtgcag ctgctccgcc agcacagcag ccctggcag  1380
gtgtacggct tcgtgcgggc ctgcctgcgc cggctggtgc cccaggcct ctggggctcc  1440
aggcacaacg aacgccgctt cctcaggaac accaagaagt tcatctccct ggggaagcat  1500
gccaagctct cgctgcagga gctgacgtgg aagatgagcg tgcgggactg cgcttggctg  1560
cgcaggagcc cagggggttgg ctgtgttccg gccgcagagc accgtctgcg tgaggagatc  1620
ctggccaagt tcctgcactg gctgatgagt gtgtacgtcg tcgagctgct caggtctttc  1680
ttttatgtca cggagaccac gtttcaaaag aacaggctct ttttctaccg gaagagtgtc  1740
tggagcaagt tgcaaagcat tggaatcaga cagcacttga gagggtgca gctgcgggag  1800
ctgtcggaag cagaggtcag gcagcatcgg gaagccaggc ccgccctgct gacgtccaga  1860
ctccgcttca tccccaagcc tgacgggctg cggccgattg tgaacatgga ctacgtcgtg  1920
ggagccagaa cgttccgcag agaaaagagg gccgagcgtc tcacctcgag ggtgaaggca  1980
ctgttcagcg tgctcaacta cgagcggcg cggcgcccg gcctcctggg cgcctctgtg  2040
ctgggcctgg acgatatcca cagggcctgg cgcaccttcg tgctgcgtgt gcgggcccag  2100
gacccgccgc ctgagctgta ctttgtcaag gtggatgtga cgggcgcgta cgacaccatc  2160
ccccaggaca ggctcacgga ggtcatcgcc agcatcatca aacccagaa cacgtactgc  2220
gtgcgtcggt atgccgtggt ccagaaggcc gccatgggc acgtccgcaa ggccttcaag  2280
agccacgtct ctaccttgac agacctccag ccgtacatgc gacagttcgt ggctcacctg  2340
caggagacca gcccgctgag ggatgccgtc gtcatcgagc agagctcctc cctgaatgag  2400
gccagcagtg gcctcttcga cgtcttccta cgcttcatgt gccaccacgc cgtgcgcatc  2460
agggggcaagt cctacgtcca gtgccagggg atcccgcagg gctccatcct ctccacgctg  2520
ctctgcagcc tgtgctacgg cgacatggag aacaagctgt ttgcggggat tcggcgggac  2580
gggctgctcc tgcgtttggt ggatgatttc ttgttggtga cacctcacct cacccacgcg  2640
aaaaccttcc tcaggaccct ggtccgaggt gtccctgagt atggctgcgt ggtgaacttg  2700
cggaagacag tggtgaactt ccctgtagaa gacgaggccc tgggtggcac ggctttttgtt  2760
cagatgccgg cccacggcct attccctggt gccggcctgc tgctggatac ccggaccctg  2820
gaggtgcaga gcgactactc cagctatgcc cggacctcca tcagagccag tctcaccttc  2880
aaccgcggct tcaaggctgg gaggaacatg cgtcgcaaac tctttggggt cttgcgggcg  2940
aagtgtcaca gcctgtttgc ggatttgcag gtgaacagcc tccagacggt gtgcaccaac  3000
atctacaaga tcctcctgct gcaggcgtac aggtttcacg catgtgtgct gcagctccca  3060
tttcatcagc aagtttggaa gaaccccaca tttttcctgc gcgtcatctc tgacacggcc  3120
tccctctgct actccatcct gaaagccaag aacgcaggga tgtcgctggg ggccaagggc  3180
gccgccggcc ctctgccctc cgaggccgtg cagtggctgt gccaccaagc attcctgctc  3240
```

```
aagctgactc gacaccgtgt cacctacgtg ccactcctgg ggtcactcag gacagcccag    3300
acgcagctga gtcggaagct cccggggacg acgctgactg ccctggaggc cgcagccaac    3360
ccggcactgc cctcagactt caagaccatc ctggacga                            3398
```

<210> SEQ ID NO 2
<211> LENGTH: 1132
<212> TYPE: PRT
<213> ORGANISM: Homo sapiens

<400> SEQUENCE: 2

```
Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350
```

```
Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
770                 775                 780
```

Pro Leu Arg Asp Ala Val Val Ile Glu Gln Ser Ser Leu Asn Glu
785                 790                 795                 800

Ala Ser Ser Gly Leu Phe Asp Val Phe Leu Arg Phe Met Cys His His
            805                 810                 815

Ala Val Arg Ile Arg Gly Lys Ser Tyr Val Gln Cys Gln Gly Ile Pro
        820                 825                 830

Gln Gly Ser Ile Leu Ser Thr Leu Leu Cys Ser Leu Cys Tyr Gly Asp
    835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
            885                 890                 895

Val Val Asn Leu Arg Lys Thr Val Asn Phe Pro Val Glu Asp Glu
        900                 905                 910

Ala Leu Gly Gly Thr Ala Phe Val Gln Met Pro Ala His Gly Leu Phe
    915                 920                 925

Pro Trp Cys Gly Leu Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
            965                 970                 975

Val Leu Arg Ala Lys Cys His Ser Leu Phe Ala Asp Leu Gln Val Asn
        980                 985                 990

Ser Leu Gln Thr Val Cys Thr Asn Ile Tyr Lys Ile Leu Leu Leu Gln
    995                 1000                1005

Ala Tyr Arg Phe His Ala Cys Val Leu Gln Leu Pro Phe His Gln Gln
    1010                1015                1020

Val Trp Lys Asn Pro Thr Phe Phe Leu Arg Val Ile Ser Asp Thr Ala
1025                1030                1035                1040

Ser Leu Cys Tyr Ser Ile Leu Lys Ala Lys Asn Ala Gly Met Ser Leu
            1045                1050                1055

Gly Ala Lys Gly Ala Ala Gly Pro Leu Pro Ser Glu Ala Val Gln Trp
        1060                1065                1070

Leu Cys His Gln Ala Phe Leu Leu Lys Leu Thr Arg His Arg Val Thr
    1075                1080                1085

Tyr Val Pro Leu Leu Gly Ser Leu Arg Thr Ala Gln Thr Gln Leu Ser
    1090                1095                1100

Arg Lys Leu Pro Gly Thr Thr Leu Thr Ala Leu Glu Ala Ala Ala Asn
1105                1110                1115                1120

Pro Ala Leu Pro Ser Asp Phe Lys Thr Ile Leu Asp
            1125                1130

<210> SEQ ID NO 3
<211> LENGTH: 3396
<212> TYPE: DNA
<213> ORGANISM: Homo sapiens

<400> SEQUENCE: 3
atgccgcgcg ctccccgctg ccgagccgtg cgctccctgc tgcgcagcca ctaccgcgag    60
gtgctgccgc tggccacgtt cgtgcggcgc ctggggcccc agggctggcg gctggtgcag   120
cgcggggacc cggcggcttt ccgcgcgctg gtggcccagt gcctggtgtg cgtgccctgg   180

```
gacgcacggc cgcccccgc cgccccctcc ttccgccagg tgtcctgcct gaaggagctg    240
gtggcccgag tgctgcagag gctgtgcgag cgcggcgcga agaacgtgct ggccttcggc    300
ttcgcgctgc tggacggggc ccgcgggggc ccccccgagg ccttcaccac cagcgtgcgc    360
agctacctgc ccaacacggt gaccgacgca ctgcggggga gcgggcgtg ggggctgctg     420 ctgcgccgcg tgggcgacga cgtgctggtt cacctgctgg cacgctgcgc gctctttgtg    480
ctggtggctc ccagctgcgc ctaccaggtg tgcgggccgc cgctgtacca gctcggcgct    540
gccactcagg cccggccccc gccacacgct agtggacccc gaaggcgtct gggatgcgaa    600
cgggcctgga accatagcgt cagggaggcc ggggtccccc tgggcctgcc agccccgggt    660
gcgaggaggc gcggggggcag tgccagccga agtctgccgt tgcccaagag gcccaggcgt    720
ggcgctgccc ctgagccgga gcggacgccc gttgggcagg ggtcctgggc ccacccgggc    780
aggacgcgtg gaccgagtga ccgtggtttc tgtgtggtgt cacctgccag acccgccgaa    840
gaagccacct ctttggaggg tgcgctctct ggcacgcgcc actcccaccc atccgtgggc    900
cgccagcacc acgcgggccc cccatccaca tcgcggccac cacgtccctg ggacacgcct    960 tgtccccgg tgtacgccga gaccaagcac ttcctctact cctcaggcga caaggagcag    1020
ctgcggccct ccttcctact cagctctctg aggcccagcc tgactggcgc tcggaggctc    1080
gtggagacca tctttctggg ttccaggccc tggatgccag ggactccccg caggttgccc    1140
cgcctgcccc agcgctactg gcaaatgcgg cccctgtttc tggagctgct gggaaccac     1200 gcgcagtgcc cctacggggt gctcctcaag acgcactgcc cgctgcgagc tgcggtcacc    1260
ccagcagccg gtgtctgtgc ccgggagaag ccccagggct ctgtggcggc cccgaggag     1320 gaggacacag acccccgtcg cctggtgcag ctgctccgcc agcacagcag cccctggcag    1380
gtgtacggct tcgtgcgggc ctgcctgcgc cggctggtgc ccccaggcct ctggggctcc    1440
aggcacaacg aacgccgctt cctcaggaac accaagaagt tcatctccct ggggaagcat    1500
gccaagctct cgctgcagga gctgacgtgg aagatgagcg tgcgggactg cgcttggctg    1560
cgcaggagcc caggggttgg ctgtgttccg gccgcagagc accgtctgcg tgaggagatc    1620
ctggccaagt tcctgcactg gctgatgagt gtgtacgtcg tcgagctgct caggtctttc    1680
ttttatgtca cggagaccac gtttcaaaag aacaggctct tttctaccg gaagagtgtc     1740 tggagcaagt tgcaaagcat tggaatcaga cagcacttga agagggtgca gctgcgggag    1800
ctgtcggaag cagaggtcag gcagcatcgg gaagccaggc cgccctgct gacgtccaga     1860 ctccgcttca tccccaagcc tgacgggctg cggccgattg tgaacatgga ctacgtcgtg    1920
ggagccagaa cgttccgcag agaaaagagg gccgagcgtc tcacctcgag ggtgaaggca    1980
ctgttcagcg tgctcaacta cgagcgggcg cggcgccccg gcctcctggg cgcctctgtg    2040
ctgggcctgg acgatatcca cagggcctgg cgcaccttcg tgctgcgtgt gcgggcccag    2100
gacccgccgc ctgagctgta ctttgtcaag gtggatgtga cgggcgcgta cgacaccatc    2160
ccccaggaca ggctcacgga ggtcatcgcc agcatcatca aacccagaa cacgtactgc     2220 gtgcgtcggt atgccgtggt ccagaaggcc gcccatgggc acgtccgcaa ggccttcaag    2280
agccacgtct ctaccttgac agacctccag ccgtacatgc gacagttcgt ggctcacctg    2340
caggagacca gcccgctgag ggatgccgtc gtcatcgagc agagctcctc cctgaatgag    2400
gccagcagtg gcctcttcga cgtcttccta cgcttcatgt gccaccacgc cgtgcgcatc    2460
aggggcaagt cctacgtcca gtgccagggg atcccgcagg gctccatcct ctccacgctg    2520
ctctgcagcc tgtgctacgg cgacatggag aacaagctgt ttgcggggat tcggcgggac    2580
```

```
gggctgctcc tgcgtttggt ggatgatttc ttgttggtga cacctcacct cacccacgcg    2640
aaaaccttcc tcaggaccct ggtccgaggt gtccctgagt atggctgcgt ggtgaacttg    2700
cggaagacag tggtgaactt ccctgtagaa gacgaggccc tgggtggcac ggcttttgtt    2760
cagatgccgg cccacggcct attcccctgg tgcggcctgc tgctggatac ccggaccctg    2820
gaggtgcaga gcgactactc cagctatgcc cggacctcca tcagagccag tctcaccttc    2880
aaccgcggct tcaaggctgg gaggaacatg cgtcgcaaac tctttggggt cttgcggctg    2940
aagtgtcaca gcctgtttct ggatttgcag gtgaacagcc tccagacggt gtgcaccaac    3000
atctacaaga tcctcctgct gcaggcgtac aggtttcacg catgtgtgct gcagctccca    3060
tttcatcagc aagtttggaa gaaccccaca ttttcctgc gcgtcatctc tgacacggcc    3120
tccctctgct actccatcct gaaagccaag aacgcaggga tgtcgctggg ggccaagggc    3180
gccgccggcc ctctgccctc cgaggccgtg cagtggctgt gccaccaagc attcctgctc    3240
aagctgactc gacaccgtgt cacctacgtg ccactcctgg ggtcactcag gacagcccag    3300
acgcagctga gtcggaagct cccggggacg acgctgactg ccctggaggc cgcagccaac    3360
ccggcactgc cctcagactt caagaccatc ctggac                              3396
```

<210> SEQ ID NO 4
<211> LENGTH: 1132
<212> TYPE: PRT
<213> ORGANISM: Homo sapiens

<400> SEQUENCE: 4

```
Met Pro Arg Ala Pro Arg Cys Arg Ala Val Arg Ser Leu Leu Arg Ser
  1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
```

```
                 225                 230                 235                 240
Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
                260                 265                 270

Val Ser Pro Ala Arg Pro Ala Glu Glu Ala Thr Ser Leu Glu Gly Ala
                275                 280                 285

Leu Ser Gly Thr Arg His Ser His Pro Ser Val Gly Arg Gln His His
                290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
                355                 360                 365

Arg Pro Trp Met Pro Gly Thr Pro Arg Arg Leu Pro Arg Leu Pro Gln
370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
                420                 425                 430

Gly Ser Val Ala Ala Pro Glu Glu Asp Thr Asp Pro Arg Arg Leu
                435                 440                 445

Val Gln Leu Leu Arg Gln His Ser Ser Pro Trp Gln Val Tyr Gly Phe
                450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
                515                 520                 525

Val Pro Ala Ala Glu His Arg Leu Arg Glu Glu Ile Leu Ala Lys Phe
                530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
                595                 600                 605

His Arg Glu Ala Arg Pro Ala Leu Leu Thr Ser Arg Leu Arg Phe Ile
                610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655
```

-continued

Arg Val Lys Ala Leu Phe Ser Val Leu Asn Tyr Glu Arg Ala Arg Arg
         660                 665                 670

Pro Gly Leu Gly Ala Ser Val Gly Leu Asp Asp Ile His Arg
         675                 680                 685

Ala Trp Arg Thr Phe Val Leu Arg Val Arg Ala Gln Asp Pro Pro
         690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Lys Pro Gln
                 725                 730                 735

Asn Thr Tyr Cys Val Arg Arg Tyr Ala Val Val Gln Lys Ala Ala His
                 740                 745                 750

Gly His Val Arg Lys Ala Phe Lys Ser His Val Ser Thr Leu Thr Asp
         755                 760                 765

Leu Gln Pro Tyr Met Arg Gln Phe Val Ala His Leu Gln Glu Thr Ser
         770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                 805                 810                 815

Ala Val Arg Ile Arg Gly Lys Ser Tyr Val Gln Cys Gln Gly Ile Pro
                 820                 825                 830

Gln Gly Ser Ile Leu Ser Thr Leu Leu Cys Ser Leu Cys Tyr Gly Asp
         835                 840                 845

Met Glu Asn Lys Leu Phe Ala Gly Ile Arg Arg Asp Gly Leu Leu Leu
         850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                 885                 890                 895

Val Val Asn Leu Arg Lys Thr Val Val Asn Phe Pro Val Glu Asp Glu
                 900                 905                 910

Ala Leu Gly Gly Thr Ala Phe Val Gln Met Pro Ala His Gly Leu Phe
         915                 920                 925

Pro Trp Cys Gly Leu Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                 965                 970                 975

Val Leu Arg Leu Lys Cys His Ser Leu Phe Leu Asp Leu Gln Val Asn
                 980                 985                 990

Ser Leu Gln Thr Val Cys Thr Asn Ile Tyr Lys Ile Leu Leu Leu Gln
         995                 1000                1005

Ala Tyr Arg Phe His Ala Cys Val Leu Gln Leu Pro Phe His Gln Gln
         1010                1015                1020

Val Trp Lys Asn Pro Thr Phe Phe Leu Arg Val Ile Ser Asp Thr Ala
1025                1030                1035                1040

Ser Leu Cys Tyr Ser Ile Leu Lys Ala Lys Asn Ala Gly Met Ser Leu
                 1045                1050                1055

Gly Ala Lys Gly Ala Ala Gly Pro Leu Pro Ser Glu Ala Val Gln Trp
         1060                1065                1070

Leu Cys His Gln Ala Phe Leu Leu Lys Leu Thr Arg His Arg Val Thr
         1075                1080                1085

-continued

```
Tyr Val Pro Leu Leu Gly Ser Leu Arg Thr Ala Gln Thr Gln Leu Ser
    1090                1095                1100

Arg Lys Leu Pro Gly Thr Thr Leu Thr Ala Leu Glu Ala Ala Ala Asn
1105                1110                1115                1120

Pro Ala Leu Pro Ser Asp Phe Lys Thr Ile Leu Asp
                1125                1130

<210> SEQ ID NO 5
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 5

Val Leu Arg Ala Lys Ser His Ser Leu Phe Ala Asp Leu Gln Cys
1               5                   10                  15

<210> SEQ ID NO 6
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 6

Arg Arg Lys Leu Phe Gly Val Leu Arg Ala Lys Cys His Ser Leu Phe
1               5                   10                  15

Ala Cys

<210> SEQ ID NO 7
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 7

Arg Arg Lys Leu Phe Gly Val Leu Arg Leu Lys Cys His Ser Leu Phe
1               5                   10                  15

Leu Asp Leu Gln Val Asn Ser Leu Gln Thr Val Cys Thr Asn
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 8

Arg Arg Lys Leu Phe Gly Val Leu Arg Ala Lys Cys His Ser Leu Phe
1               5                   10                  15

Ala Asp Leu Gln Val Asn Ser Leu Gln Thr Val Cys Thr Asn
            20                  25                  30
```